US008592375B2

(12) United States Patent
Yeaman et al.

(10) Patent No.: US 8,592,375 B2
(45) Date of Patent: Nov. 26, 2013

(54) MULTIFUNCTIONAL CONTEXT-ACTIVATED PROTIDES AND METHODS OF USE

(75) Inventors: Michael R. Yeaman, Redondo Beach, CA (US); Nannette Y. Yount, San Juan Capistrano, CA (US); John E. Edwards, Jr., Palos Verdes, CA (US); Eric P. Brass, Palos Verdes, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 907 days.

(21) Appl. No.: 10/524,952

(22) PCT Filed: Aug. 20, 2003

(86) PCT No.: PCT/US03/26405
§ 371 (c)(1),
(2), (4) Date: Jan. 5, 2006

(87) PCT Pub. No.: WO2004/017985
PCT Pub. Date: Mar. 4, 2004

(65) Prior Publication Data
US 2006/0135416 A1    Jun. 22, 2006

Related U.S. Application Data

(63) Continuation of application No. 10/225,562, filed on Aug. 20, 2002, now Pat. No. 7,067,621.

(51) Int. Cl.
*A61K 38/00* (2006.01)
*A61P 17/00* (2006.01)
*A61P 29/00* (2006.01)
*A61P 31/04* (2006.01)
*A01N 37/18* (2006.01)

(52) U.S. Cl.
USPC .......................................... 514/18.7; 514/2.4

(58) Field of Classification Search
None
See application file for complete search history.

(56) References Cited

U.S. PATENT DOCUMENTS

| | | | |
|---|---|---|---|
| 5,268,154 A | 12/1993 | Pepi | |
| 5,420,109 A | 5/1995 | Suto | |
| 5,506,206 A | 4/1996 | Kozarich | |
| 5,593,866 A * | 1/1997 | Hancock et al. | 435/69.7 |
| 5,686,416 A | 11/1997 | Kozarich | |
| 5,752,515 A | 5/1998 | Jolesz | |
| 5,789,542 A | 8/1998 | McLaughlin | |
| 5,851,802 A * | 12/1998 | Better | 435/69.7 |
| 7,067,621 B2 * | 6/2006 | Yeaman et al. | 530/324 |
| 7,754,676 B2 * | 7/2010 | Kwak et al. | 514/19.3 |
| 2004/0116348 A1 * | 6/2004 | Chau et al. | 514/12 |

FOREIGN PATENT DOCUMENTS

WO    WO 99/42119    8/1999

OTHER PUBLICATIONS

Sorensen et al. Fragmentation of proteins by *S. aureus* strain V8 protease. FEBS 10460, 1991, vol. 294, No. 3, pp. 195-197.*
Achilles, K., "Coumarin Derivatives as Protease-Sensitive Prodrugs," *Arch. Pharm. Pharm. Med. Chem.* 334:209-215 (2001).
Alvarez-Bravo et al., "Novel synthetic antimicrobial peptides effective against methicillin-resistant *Staphylococcus aureus*," *Biochem. J.* 302:535-538 (1994).
*Annual Reports in Medicinal Chemistry*. Eds. Blondelle and Houghten. San Diego: Academic Press, 159-168.
Bessalle, R. "All-D-magainin: chirality, antimicrobial activity and proteolytic resistance" *FEBS Lett.* 274:151-155 (1990).
Blondelle SE, Houghten RA, "Design of model amphipathic peptides having potent antimicrobial activities," *Biochem.* 31: 12688-12694 (1992).
Bodanzsky, M. *Principles of Peptide Synthesis* 1st ed., and 2nd rev. ed. New York: Springer-Verlag, 1984 & 1994, Ch. 7.
Brem, H., et al., "Interstitial chemotherapy with drug polymer implants for the treatment of recurrent gliomas" *J. Neurosurg* 74: 441-446 (1991).
*Burger's Medicinal Chemistry and Drug Discovery* vol. 1. Ed. M.E. Wolff. John Wiley & Sons, 1995, 619-620.
*Combinatorial Chemistry*. Eds. Wilson and Czarnick. New York: John Wiley & Sons, 235, 1997.
Davioud-Charvet et al., "A Prodrug Form of a Plasmodium falciparum Glutathione Reductase Inhibitor Conjugated with a 4-Anilinoquinoline," *J. Med. Chem.* 44:4268-4276 (2001).
Dhawan et al., "In Vitro Resistance to Thrombin-Induced Platelet Microbicidal Protein Is Associated with Enhanced Progression and Hematogenous Dissemination in Experimental *Staphylococcus aureus* Infective Endocarditis," *Infect and Immun* 66:3476-3479 (1998).
Expand, *The Amphipathic Helix* Boca Raton: CRC Press, 1993.
Fields et al., "A Salmonella Locus That Controls Resistance to Microbicidal Proteins from Phagocytic Cells," *Science* 243:1059-1062 (1989).
Friedrichsen et al., "Application of Enzymatically Stable Dipeptides for Enhancement of Intestinal Permeability. Synthesis and In Vitro Evaluation of Dipeptide-Coupled Compounds," *Bioorg Med Chem.* 9:2625-2632 (2001).
Garsky et al., "The Synthesis of a Prodrug of Doxorubicin Designed to Provide Reduced Systemic Toxicity and Greater Target Efficacy," *J. Med. Chem.* 44:4216-4224 (2001).

(Continued)

*Primary Examiner* — Marcela M Cordero Garcia
(74) *Attorney, Agent, or Firm* — Jones Day

(57) ABSTRACT

This invention is directed to multifunctional, context-activated protides that have two or more effectors with individually distinct biological functions and one or more corresponding activator sites that can each initiate or amplify the biological function of one or more effectors upon context-activation. The context-activated protides of the invention are useful in the diagnosis, prophylaxis, and therapy of a broad range of pathological conditions.

10 Claims, 13 Drawing Sheets

(56) References Cited

OTHER PUBLICATIONS

Goodman and Ro, "Peptidometics for Drug Design," *Burger's Medicinal Chemistry and Drug Discovery* vol. 1. Ed. M.E. Wolff. John Wiley & Sons, 1995, 803-861.

Han and Amidon, "Targeted Prodrug Design to Optimize Drug Delivery,"*AAPS Pharmsci.* 2:1-11 (2000).

Javadpour et al., "De novo antimicrobial peptides with low mammalian cell toxicity," *J. Med. Chem.* 39:3107-3113 (1996).

Kreuter, J., et al. "Passage of peptides through the blood-brain barrier with colloidal polymer particles (nanoparticles)," *Brain Res.* 674:171-174 (1995).

Lackey et al., "Enzyme-catalyzed therapeutic agent (ECTA) design: activation of the antitumor ECTA compound NB1011 by thymidylate synthase," *Biochemical Pharmacology* 61:179-189 (2001).

Li et al., "NB2001, a Novel Antibacterial Agent with Broad-Spectrum Activity and Enhanced Potency against ÿ-Lactamase-Producing Strains," *Antimicrobial Agents and Chemotherapy* 46:1262-1268 (2002).

Li et al., "A Novel Approach to Thymidylate Synthase as a Target for Cancer Chemotherapy," *Molecular Pharmacology* 59: 446-452 (2001).

Liang et al., "Attempts: a heparin/protamine-based delivery system for enzyme drugs," *Journal of Controlled Release* 78:67-79 (2002).

Lipka et al, "Transmembrane transport of peptide type compounds: Prospects for oral delivery," *Journal of Controlled Release* 39:121-129 (1996).

*Liposome Technology* vols. 1-3, 2nd Edn. Ed. Gregoriadis, G. Boca Raton, FL: CRC Press, 1993.

Lugtenberg and van Alphen, "Molecular architecture and functioning of the outer membrane of *Escherichia coli* and other gram-negative bacteria," *Biochim Biophys Acta.* 737:51-115 (1983).

Maloy and Kari, "Structure-Activity Studies on Magainins and Other Host Defense Peptides," *Biopolymers* 37:105-122 (1995).

Mancheño, J.M., et al., "A peptide of nine amino acid residues from alpha-sarcin cytotoxin is a membrane-perturbing structure," *J. Peptide Res.* 51:142-148 (1998).

Pestonjamasp et al., "Processing site and gene structure for the murine antimicrobial peptide CRAMP," *Peptides* 22:1643-1650 (2001).

Roberts, and Vellaccio, *The Peptides: Analysis, Synthesis, Biology* vol. 5. Ed. Gross and Meinhofer. New York: Academic Press, 1983, 341.

Silva et al., "Potential Tuberculostatic Agents: Micelle-Forming Copolymer Poly (ethylene glycol)-Poly (aspartic acid) Prodrug with Isoniazid," *Arch. Pharm. Pharm. Med. Chem.* 334:189-193 (2001).

Stewart and Young, *Solid Phase Peptide Synthesis* 2nd ed. Rockford, Ill: Pierce Chemical Co., 1984.

*The Merck Manual.* 16th Edn. Ed. Berkow, R.Rahway, N.J.: Merck Publishing, 1992.

Yeaman and Bayer, "Antimicrobial peptides from platelets," *Drug Resistance Updates* 2:116-126 (1999).

Yeaman et al., "Partial Characterization and Staphylocidal Activity of Thrombin-Induced Platelet Microbicidal Protein," *Infection and Immunity* 60:1202-1209 (1992).

Yeaman, et al., "Resistance to Platelet Microbicidal Protein Results in Increased Severity of Experimental *Candida albicans* Endocarditis," *Infection and Immunity* 64:1379-1384 (1996).

Yeaman, et al., *38th Interscience Conference on Antimicrobial Agents* San Diego, CA Abstract No. F-170 (1999).

Yeaman, M., "The Role of Platelets in Antimicrobial Host Defense," *Clinical Infectious Diseases* 25:951-968 (1997).

\* cited by examiner

General Examples: Effector$_1$ / Effector$_n$ Mosaic

| Effector 1 | Activator | Effector 2 |
|---|---|---|
| Antimicrobial | LPXTG | Antimicrobial |
| Anti-Toxicity | Signal Process | Antimicrobial |
| Immunomodulate | Thrombin | Antimicrobial |
| Antiangiogenesis | MtPase | Immunomodulate |
| Apoptosis | Mitochondrial | Antiangiogenesis |

Note: many other permutations on the mosaic concept;
Activator may also be non-protease (eg., esterase) sites

FIGURE 6A

Examples of Activators

Specific

Thrombin
Bradykinin
C4b2a
C3bBb
Elastase
Metalloproteinase

General

Clotting Cascade Proteases
Complement Fixing Proteases
Tumor-Specific Proteases

Examples of Effectors

Specific

Defensins (alpha, beta, theta)
Cecropins, Magainins
Protegrins, Indolicidins
HIV Viral protein R (VPR)
Tissue factors; angiogenesis
RP-like peptides; other APs

General

Antimicrobial peptides
Immunomodulatory peptides
Antitumor peptides; others

FIGURE 6B

| Name | Sequence | Activator | |
|---|---|---|---|
| PT-1 | AKELRCQCIKTYSKE▼ALYKKFKKKLLKSLKRLG<br>[IL-8 Chemokine Motif]   [ Antimicrobial Peptide Domain ] | V8 Protease | SEQ ID NO: 1 |
| PT-2 | AKELRCQCIKTYSKLAR▼SALYKKFKKKLLKSLKRLG<br>[IL-8 Chemokine Motif]       [ Antimicrobial Peptide Domain ] | C3 Convertase | SEQ ID NO: 2 |
| PT-3 | AKELRCQCIKTYSKLVPR▼GSALYKKFKKKLLKSLKRLG<br>[IL-8 Chemokine Motif]         [ Antimicrobial Peptide Domain ] | Thrombin | SEQ ID NO: 3 |
| PT-4 | AKELRCQCIKTYSKPQGIAG▼QALYKKFKKKLLKSLKRLG<br>[IL-8 Chemokine Motif]             [ Antimicrobial Peptide Domain ] | MMP-9 | SEQ ID NO: 4 |

Key: ▼ denotes activator-specific cleavage site

FIGURE 12

MULTIFUNCTIONAL CONTEXT-ACTIVATED PROTIDES AND METHODS OF USE

BACKGROUND OF THE INVENTION

This invention relates generally to molecular medicine and, more specifically, to context-activated multifunctional protides.

Treatment of many diseases can be severely limited by suboptimal distribution and/or indiscriminant toxicity of the therapeutic agent, and by resistance of the pathogenic target cells or tissue(s) to the chosen therapeutic drug. Drug resistance is a burgeoning and international problem of daunting concern in the treatment of infectious diseases, cancer, and other medical conditions.

The number of new diagnoses each year of all cancer types combined continues to increase. Although cancer drugs can be effective against metastatic disease, their mechanism of action often leads to the survival of drug-resistant tumors and drug toxicity with fatal consequences to the patient. For example, chemotherapy, while generally an effective treatment against human cancerous diseases, is hampered when the specific tumor cell-type becomes resistant to the chemotherapeutic. Overall, one of the greatest limitations on the efficacy of cancer chemotherapeutic agents is the tendency of cancer cells to develop broad-spectrum resistance to a diverse panel of anti-cancer and cytotoxic drugs. Such multiple drug resistance (MDR) is believed to occur to varying degrees in most cancers, either from the onset of the cancer or on recurrence following chemotherapy.

Like cancer, infectious diseases due to pathogenic bacteria, fungi, protozoa and viruses are leading causes of death worldwide. Moreover, the emergence of drug-resistant forms of these pathogens has created an urgent need for new and more effective approaches and anti-infective agents to combat the growing threat of microbial drug-resistance.

Microbes often become resistant to antibiotics and/or non-antibiotic agents. Many conventional antibiotics retard pathogen proliferation by interacting with and/or entering the microbes and interfering with the elaboration of microbial components or pathways needed for macromolecular metabolism (eg., proteins or nucleic acids), cellular regulation, or reproduction. For example, many conventional antibiotics function by impairing DNA replication or expression, transcription, ribosome function, translation, or cell wall or membrane integrity. The majority of available anti-infective agents inhibit intracellular targets within pathogenic microorganisms. Antibiotic resistance typically involves individual or multiple point mutations that slightly change the structure of the antibiotic target, for example, the cell wall synthetic enzymes or ribosomal subunit proteins, such that the antibiotic is no longer effective. Such a slight change in target structure with no detrimental effect on function can be sufficient to reduce or eliminate antibiotic inhibition of the target, translating to reduced or abrogated efficacy of the anti-infective agent. Other common mechanisms for the rapid development of resistance to conventional antibiotics include, for example, degradation of the antibiotic prior to target inhibition, reduced permeability or access of the antibiotic to its target, and/or increased export of the antibiotic by the resistant organism. Thus, antibiotic resistance can occur by the acquisition of genes encoding enzymes that inactivate agents, modify the target of the agent, or result in impermeability or active efflux of the agent. Improved methods for controlling drug resistance in microbes, in particular, microbes that are highly drug resistant, would be of tremendous benefit.

Thus, there exists a need for therapeutic agents that circumvent or have reduced susceptibility to common mechanisms of drug resistance among pathogenic cells, including agents of infectious disease and cancer. The present invention satisfies this need and provides related advantages as well.

SUMMARY OF THE INVENTION

This invention is directed to multifunctional, context-activated protides that have two or more effectors with individually distinct biological functions and one or more corresponding activator sites that can each initiate or amplify the biological function of one or more effectors upon context-activation. The context-activated protides of the invention are useful in the diagnosis, prophylaxis, and therapy of a broad range of pathological conditions.

BRIEF DESCRIPTION OF THE DRAWINGS

FIG. 6 shows (A) examples of several permutations of effector biological functions and activators useful in preparing invention protides; and (B) a table setting forth further examples of general and specific effectors and activators useful for the preapration of an invention protide.

FIG. 12 shows the amino acid sequence of PT-1 (SEQ ID NO: 1), PT-2 (SEQ ID NO: 2), PT-3 (SEQ ID NO: 3) and PT-4 (SEQ ID NO: 4).

DETAILED DESCRIPTION OF THE INVENTION

Figure 1:
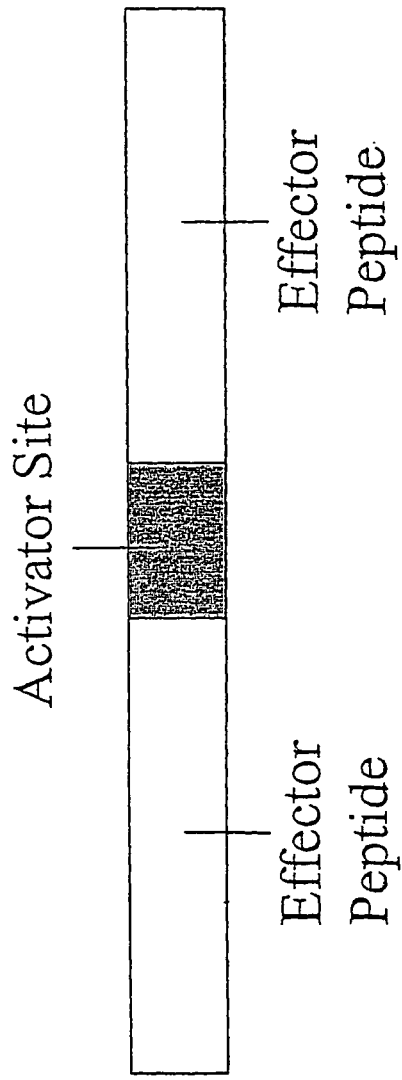
FIG. 1 shows the general conceptual scheme for an invention protide.
Figure 2:
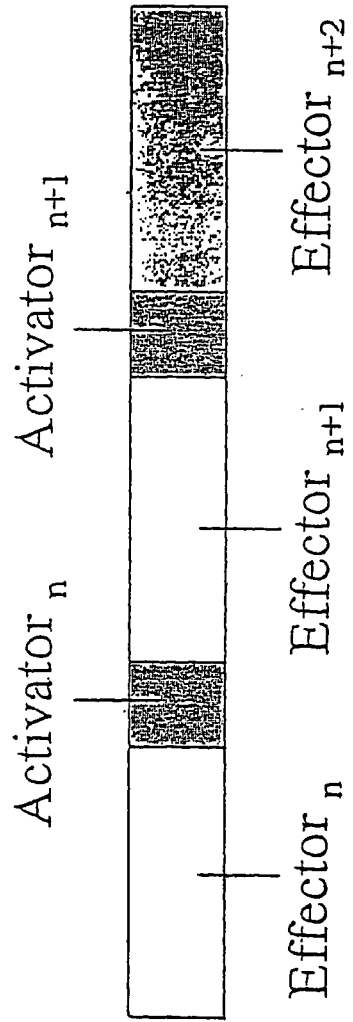
FIG. 2 shows an extrapolated conceptual scheme for an invention protide having more than one activator site and more than two effectors.

This invention is directed to multifunctional, context-activated protides that have two or more effectors with individually distinct biological functions and one or more corresponding activator sites that can each initiate or amplify the biological function of one or more effectors upon context-activation. The context-activated protides of the invention are useful in the diagnosis, prophylaxis, and therapy of a broad range of pathological conditions."

In particular, the invention protides provide novel agents and strategies to target diagnostic, prophylactic, and/or therapeutic agents to specific sites, to minimize cytotoxicity of otherwise toxic agents, to create relevant gradients for recruitment, potentiation, suppression, or other desirable modulation of immune system or other structural, effector or regulatory cells, and further provide many other applications for diagnosis, imaging, localization, prevention, or treatment of disease, or as research tools to investigate areas including pathogenesis, physiology, immunobiology, cell regulation, gene expression, or other disciplines.

The invention protides have two or more distinct biological functions and are designed to be activated within a defined or characteristic context. Invention protides have the advantage of designs that can be customized, engineered, chosen, or combined to allow for highly selective correspondence to or association with or unique to a specific pathological condition or etiology. The distinct biological functions can further be associated with distinct functional aims, for example, therapy, prevention, amplification and detoxification. As described herein, a multifunctional, context-activated protide can be designed to be activated in any context desired by the user, a feature which makes the invention protides useful to applications in many areas of medicine and biomedical research, including, for example, diagnosis, imaging, detection, speciation or other specification, prevention/prophylaxis, and therapy of a wide range of pathological conditions such as infectious diseases, neoplastic diseases, immune and autoimmune disorders, cardiovascular conditions, disorders in metabolism or physiology, diseases of inheritance or genetic abnormality, a variety of pathological conditions associated with gene expression, mitochondrial dysfunction or regulation, as well as cell death and/or cellular senescence.

A pathological condition appropriate for treatment with a protide can be a symptomatic disease or other abnormal condition or injury of a mammalian cell or tissue. Such pathological conditions include, for example, hyperproliferative and unregulated neoplastic cell growth, degenerative conditions, inflammatory diseases, autoimmune diseases and infectious diseases. Hyperplastic and cancer cells proliferate in an unregulated manner, causing destruction of tissues and organs. Specific examples of hyperplasias include benign prostatic hyperplasia and endometrial hyperplasia. Specific examples of cancer include prostate, breast, ovary, lung, uterus, brain and skin cancers.

Abnormal cellular growth can also result from infectious diseases in which foreign organisms cause excessive growth. For example, human papilloma viruses can cause abnormal growth of tissues. The growth of cells infected by a pathogen is abnormal due to the alteration of the normal condition of a cell resulting from the presence of a foreign organism. Specific examples of infectious diseases include DNA and RNA viral diseases, bacterial diseases, fungal diseases, and protozoal or parasitic diseases. Similarly, the cells mediating autoimmune and inflammatory diseases are aberrantly regulated which results in, for example, the continued proliferation and activation of immune mechanisms with the destruction of tissues and organs. Specific examples of autoimmune diseases include, for example, rheumatoid arthritis and systemic lupus erythematosis. Specific examples of degenerative disease include osteoarthritis and Alzheimer's disease.

By specific mention of the above categories of pathological conditions, those skilled in the art will understand that such terms include all classes and types of these pathological conditions. For example, the term cancer is intended to include all known cancers, whether characterized as malignant, benign, soft tissue or solid tumors, or hematologic tumors relating to cells in circulation, such as leukemias. Similarly, the terms infectious diseases, degenerative diseases, autoimmune diseases and inflammatory diseases are intended to include all classes and types of these pathological conditions. Those skilled in the art will know the various classes and types of proliferative, infectious, autoimmune and inflammatory diseases.

As described below, in addition to their direct antimicrobial efficacies, the invention protides are useful based on their ability to circumvent or minimize conventional resistance mechanisms by pathogens or tumor cells. For example, this can be the result of activation by activators that are present outside of the target cell such that the protide need not necessarily enter the target cell to be activated and to achieve subsequent efficacy, thus minimizing the likelihood for resistance due to reduced target access or increased efflux of the protide. Furthermore, in many conventional resistance mechanisms, resistance can be induced by the presence of the anti-infective agent itself. Protides can be designed to be activated by such microbial counter-responses or virulence factors. Thus, the more of the activator that is made by the organism, the more protide activation results, yielding an expected amplification of the anti-pathogenic efficacy of the protide. Conversely, decreased production of the activators can translate in turn to decreased presence or function of these same activators such as virulence factors or mediators of pathogenesis, in essence turning off the pathogenic potential of the target cell, or reducing its ability to protect itself from otherwise normal host defenses. Similarly, protides can be beneficial by reconstituting tumor cell or microbial pathogen susceptibility to conventional therapeutic agents, to which these pathogenic cells would otherwise be resistant. Thus, the invention protides can either be activated from upregulation of resistance- or virulence factor expression, or can impact efficacy by effecting the downregulation of virulence factor expression by pathogenic cells or organisms.

The invention provides a context-activated protide encompassing the amino acid sequence set forth as SEQ ID NO: 1 and referred to herein as "PT-1," which includes two effectors and one activator. Also provided by the invention is a nucleic acid sequence that encodes the amino acid corresponding to PT-1, which is set forth as SEQ ID NO: 1.

PT-1 encompasses an antimicrobial peptide effector (RP-1), a chemokine-like peptide effector (IL-8 domain), and an activator site specific for staphylococcal V8 protease, one of numerous virulence factors that is elaborated by S. aureus in order to establish and proliferate infection. As described in the example set forth below, PT-1 is cleaved into two distinct effectors in the presence of the activator, staphylococcal V8 protease. In particular, PT-1 exerts antimicrobial activity less than that of the antimicrobial peptide RP-1 in the absence of V8 protease, but antimicrobial activity equivalent to or exceeding that of RP-1 in the presence of V8 protease produced by S. aureus. Thus, PT-1 exerts optimal antimicrobial activity in the context of V8 protease as would be present in the setting of infections due to staphylococcal cells.

The invention also provides a context-activated protide encompassing the amino acid sequence set forth as SEQ ID NO: 2 and referred to herein as "PT-2," which includes two effectors and one activator. Also provided by the invention is a nucleic acid sequence that encodes the amino acid corresponding to PT-1, which is set forth as SEQ ID NO: 2.

PT-2 encompasses an antimicrobial peptide effector (RP-1), a chemokine-like peptide effector (IL-8 domain), and an activator site specific for C3 convertase, a complement fixing protease. As described herein, PT-2 is cleaved into two distinct effectors in the presence of the activator, C3 convertase.

In particular, PT-2 exerts antimicrobial activity less than that of the antimicrobial peptide RP-1 in the absence of C3 convertase, but antimicrobial activity equivalent to or exceeding that of RP-1 in the presence of C3 convertase. Thus, PT-2 exerts optimal antimicrobial activity in the context of activation of one of the three complement pathways that make up the complement system, which is part of the innate immune response to antigen exposure.

The invention further provides a context-activated protide encompassing the amino acid sequence set forth as SEQ ID NO: 3 and referred to herein as "PT-3," which includes two effectors and one activator. Also provided by the invention is a nucleic acid sequence that encodes the amino acid corresponding to PT-3, which is set forth as SEQ ID NO: 3.

PT-3 encompasses an antimicrobial peptide effector (RP-1), a chemokine-like peptide effector (IL-8 domain), and an activator site specific for thrombin, a serine-protease produced in the local context of vascular injury or infection. As herein, PT-3 is cleaved into two distinct effectors in the presence of the activator, thrombin. In particular, PT-3 exerts antimicrobial activity less than that of the antimicrobial peptide RP-1 in the absence of thrombin, but antimicrobial activity equivalent to or exceeding that of RP-1 in the presence of thrombin. Thus, PT-3 exerts optimal antimicrobial activity in the context of thrombin as would be present in the setting of vascular injury or infection.

Also provided by the invention is a context-activated protide encompassing the amino acid sequence set forth as SEQ ID NO: 4 and referred to herein as "PT-4," which includes two effectors and one activator. Also provided by the invention is a nucleic acid sequence that encodes the amino acid corresponding to PT-4, which is set forth as SEQ ID NO: 4.

PT-4 encompasses an antimicrobial peptide effector (RP-1), a chemokine-like peptide effector (IL-8 domain), and an activator site specific for the matrix metalloproteinase MMP-9, which is produced to dissolve the tissue in front of the growing blood vessel tip to allow for its continued tissue invasion. As described herein, PT-4 is cleaved into two distinct effectors in the presence of the activator, MMP-9. In particular, PT-4 exerts antineoplastic and/or antimicrobial activity less than that of the antineoplastic and/or antimicrobial activity of the peptide RP-1 in the absence of MMP-9, but antineoplastic and/or antimicrobial activity equivalent to or exceeding that of RP-1 in the presence of MMP-9. Thus, PT-4 exerts optimal antineoplastic and/or antimicrobial activity in the context of new blood vessel formation.

In a further embodiment, the invention provides a context-activated protide having at least one activator site and two or more effectors with distinct biological functions. The term "protide," as used herein, refers to a mosaic molecule composed of two or more peptide or non-peptide peptide functional domains, referred to as effectors, and one or more corresponding activator sites. A protide can consist of an indefinite number of effector and activator domains that can vary in function, activation, position, continuity, or sequence. One example of a protide described herein is PT-1 (SEQ ID NO: 1), which consists of an antimicrobial peptide effector (RP-1), a chemokine-like peptide effector (IL-8 domain), and an activator site specific for staphylococcal V8 protease.

A protide of the invention can be useful in a variety of applications relating to, for example, diagnosis, prophylaxis, or therapy of a pathological condition. It is understood that minor modifications can be made without destroying protide activity and that only a portion of, for example, a particular effector or activator site can be required in order to effect activity. Such modifications are included within the meaning of the term protide. Further, various molecules can be attached to invention protides, including for example, conventional or newly discovered synthetic anti-infective agents, conventional or newly-discovered anti-neoplastic agents, other polypeptides, carbohydrates, nucleic acids or lipids. Such modifications also are included within the definition of the term.

Minor modifications of a protide of the invention include, for example, conservative substitutions of naturally occurring amino acids and as well as structural alterations which incorporate non-naturally occurring amino acids, amino acid analogs and functional mimetics. For example, a Lysine (Lys) residue is considered to be a conservative substitution for the amino acid Arg. A protide containing one or more mimetic structures having a similar charge and spatial or steric arrangements as the reference amino acid residues is included within the definition of the term so long as the protide containing the mimetic portion exhibits a similar or enhanced activity as compared with the reference protide. It is thus understood that an invention protide includes such mimetics as chemically modified peptides, peptide-like molecules containing non-naturally occurring amino acids, and peptoids, which are peptide-like molecules resulting from oligomeric assembly of N-substituted glycines, with similar or enhanced activity as compared with the reference protide upon which the mimetic is derived or having any other property desired by the user, for example, enhanced biostability (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861), which is incorporated herein by reference in its entirety.

A variety of peptidomimetics are known in the art including, for example, peptide-like molecules that contain a constrained amino acid, a non-peptide component that mimics peptide secondary structure, or an amide bond isostere. A peptidomimetic that contains a constrained, non-naturally occurring amino acid can include, for example, an $\alpha$-methylated amino acid; an $\alpha,\alpha$-dialkyl-glycine or $\alpha$-aminocycloalkane carboxylic acid; an N$\alpha$-C$\alpha$ cylized amino acid; an N$\alpha$-methylated amino acid; a $\beta$- or $\gamma$-amino cycloalkane carboxylic acid; an $\alpha,\beta$-unsaturated amino acid; a $\beta,\beta$-dimethyl or $\beta$-methyl amino acid; a $\beta$-substituted-2,3-methano amino acid; an N-C$\delta$ or C$\alpha$-C$\delta$ cyclized amino acid; or a substituted proline or another amino acid mimetic. In addition, a peptidomimetic that mimics peptide secondary structure can contain, for example, a nonpeptidic $\beta$-turn mimic; $\gamma$-turn mimic; mimic of $\beta$-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that an invention protide can encompass these and other peptidomimetics. Likewise, an invention protide also can contain stereoisomeric amino acids or other effector or activator constituents, such as dextrorotatory (D) versions of amino acids.

As described herein, a protide can contain naturally occurring and non-naturally occurring amino acids as well as amino acid analogs and mimetics. Naturally occurring amino acids include the 20 levorotatory(L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like. Amino acid analogs include modified forms of naturally and non-naturally occurring amino acids. Such modifications can include, for example, substitution or replacement of chemical groups and moieties on the amino acid or by derivitization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the α-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics useful for preparation of an invention protide.

Specific examples of amino acid analogs and mimetics can be found described in, for example, Roberts and Vellaccio, *The Peptides: Analysis, Synthesis, Biology*, Eds. Gross and Meinhofer, Vol. 5, p. 341, Academic Press, Inc., New York, N.Y. (1983), the entire volume of which is incorporated herein by reference. Other examples include peralkylated amino acids, particularly permethylated amino acids. See, for example, *Combinatorial Chemistry*, Eds. Wilson and Czarnik, Ch. 11, p. 235, John Wiley & Sons Inc., New York, N.Y. (1997), which is incorporated herein by reference in its entirety. Yet other examples include amino acids whose amide portion and, therefore, the amide backbone of the resulting peptide, has been replaced, for example, by a sugar ring, steroid, benzodiazepine or carbo cycle. See, for example, *Burger's Medicinal Chemistry and Drug Discovery*, supra, Ch. 15, pp. 619-620, which is incorporated herein by reference in its entirety. Methods for synthesizing peptides, polypeptides, peptidomimetics and proteins are well known in the art (see, for example, U.S. Pat. No. 5,420,109; M. Bodanzsky, *Principles of Peptide Synthesis* (1st ed. & 2d rev. ed.), Springer-Verlag, New York, N.Y. (1984 & 1993), see Chapter 7; Stewart and Young, *Solid Phase Peptide Synthesis*, (2d ed.), Pierce Chemical Co., Rockford, Ill. (1984), each of which is incorporated herein by reference in its entirety).

The term "context-activated," as used herein in reference to a protide of the invention, refers to the initiation, activation or amplification of a biological or other desired, for example, diagnostic or prophylactic function of one or more protide effectors in a particular temporal, spatial, pathological and/or biochemical context. Context-activation can be initiated by direct or indirect interaction between a protide activator site and a corresponding activator that is selectively associated with the particular context. As used herein, context-activation encompasses activation in a wide variety of contexts that can include, for example, local, regional, systemic, and/or temporal proximity; as well as the presence or absence of an etiological agent, pathologic condition, or characteristic components thereof.

Thus, context need not be limited to a place, time or quality, but also can be the presence or absence of an activator, for example, an enzyme elaborated by an organism such as, for example, a specific strain of bacteria. The context for activation can consequently be of any breadth desired by the user, for example, can target a class of organisms or cell types, for example, by using an activator that is ubiquitous to the targeted class, or can alternatively have a more narrow focus by using an activator that represents a more narrowly defined target, for example, a particular genus, organism, species, subspecies, strain, or cell or tissue type. The context can be associated with a pathological condition, but also can be selected to represent a non-pathological environment, for example, in prophylactic applications of the invention practiced to preserve a normal or homeostatic condition.

As used herein, the term "effector" refers to the peptide or non-peptide functional domains of an invention protide that have specific individual functions, which are initiated or amplified upon activation and achieve specific functions relating to the diagnosis, prevention, or treatment of a disease. As described herein, an invention protide has at least two effector domains with distinct, complementary and/or synergistic biological functions. An effector is inactive or exhibits relatively reduced or attenuated biological activity unless an activator, by virtue of either its presence or absence, alters or facilitates or allows the altering of its corresponding activator site and, as a result, initiates or amplifies the diagnostic, prophylactic, therapeutic, or other biological function(s) of the effector(s). Multiple effectors can be induced by the same activator site. Peptide and non-peptide effectors can be present in the same protide, which can be referred to as a hybrid protide. Similarly, a protide can consist exclusively of peptide effectors, also referred to as a peptide protide. Similarly, a protide of the invention can consist exclusively of non-peptidic effectors. The biological function(s) of an effector that corresponds to an invention protide can be, for example, antimicrobial, immunomodulatory, pro- or anti-inflammatory, tumoricidal, pro- or anti-apoptotic, pro- and anti-angiogenic and/or hemolytic.

As described herein, a protide of the invention can be bifunctional or multifunctional, with two or more unique complementary effectors, and one or more activators as determined by specific effector and activator site domains engineered into the mosaic protide, which can be activated by specific molecules or conditions present in unique or strategic contexts of interest. Examples of such effectors can include one or more antimicrobial, anti-neoplastic, anti-inflammatory, immunomodulatory, or other peptide or non-peptide functional domains, or combinations thereof.

As used herein, the term "activator site" when used in reference to a protide of the invention, refers to a domain of the protide that, in the presence of an activator, initiates, promotes, amplifies or modulates the specific biological function of one or more effectors. As described herein, an activator site can be modified, cleaved, processed or otherwise altered in the presence of an activator. In addition, an activator site can be sensitive either to the absolute presence or absence of an activator as well as can be sensitive to a threshold concentration of an activator rather than its mere presence.

An activator site useful in the invention can include one or more sites for cleavage, modification, processing or other triggering by strategic activators, which can be, for example, proteases, esterases, lipases, or other endogenous enzymatic activators or cascades generated by or associated with a specific condition such as, for example, the presence of pathogenic microorganisms, damaged or inflamed tissues, or hematologic or solid neoplastic or pre-neoplastic cells or tumors. Such an activator site also can be selected to exploit contexts associated with biochemical or physical conditions such as requisite acidity or alkalinity, for example, acidic phagolysomes containing intracellular bacteria or fungi; or ionic or osmotic strength, for example, in a renal context, that represent a specific pathologic or non-pathologic context.

Furthermore, an activator site can be selected to exploit normal rather than a pathologic context.

An activator site can be subject to proteolytic as well as non-proteolytic activation. For example, the activator site can be located within the peptide moiety, and require a protease activator. In other embodiments, the non-proteolytic activator can target a non-proteinaceous substrate component of the protide. For example, a protide of the invention can include an esterase activator and can link peptide and/or non-peptide moieties (eg. a protide consisting of peptide and conventional antibiotic effectors) by means of an ester bond. Other biochemically relevant bonds or linkages that can serve as activation sites in an invention protide can include, for example, lipase- (lipid cleaving), nuclease- (nucleic acid cleaving), and kinase or phosphatase- (phosphate addition or removal) sensitive activators that target substrates other than peptides. For example, certain microbial pathogens or tumor cells can express, or abnormally express restriction enzymes that can provide a suitable basis for design of a protide that could be activated only within the target cell, further reducing indiscriminant host cytotoxicity.

As used herein, the term "activator" refers to a molecule or condition that, by altering the activator site, causes the liberation or onset of a specific diagnostic or biological function of effector(s). As described herein, an activator can be a normal or abnormal exogenous or endogenous cell, structure or molecule, a condition or milieu (normal or abnormal), or a combination thereof that is associated with a specific context in which activation of the protide is desired. Thus, an activator can be selected based on its presence in a temporal, spatial, or physiological context, which can be normal or abnormal, that is associated with the desired context for protide activation. An activator can consequently include physiological conditions including, for example, acidity, alkalinity, conditions of oxidation or reduction, and/or ionic and/or osmotic strength, that are associated with a particular context, and modulate protide activation. Alternatively, an activator can be a structure or molecule, for example, an enzyme, that is present in a particular spatial, temporal or pathological context. The activator molecule can modify the activator site upon association, for example, by cleavage or other modification that results in activation in the particular context, or can facilitate interaction between protide and activator(s). The activator molecule can be an enzyme including, for example, protease, esterase, lipase, nucleases or peptidase.

In one embodiment of the invention, an activator site can encompass one or more domains for cleavage, modification, processing or any other type of liberation by an activator, for example, a protease, esterase, lipase or other endogenous or exogenous enzymatic activator or cascade. The choice of one or more activator sites that correspond to specific activators depends directly on the desired context for activation. Thus, an activator can be a particular pathologic setting or condition that is chosen based on its association with a particular etiological agent or host response. In the presence of the activator, one or more effectors are liberated so as to achieve a specific function relating to, for example, the treatment, prevention, or diagnosis of a targeted disease. An activator site can thus be strategically designed to become activated in temporal and spatial proximity to activator expression, thereby allowing the activation of a protide to be targeted to a particular context and over time so as to maximize the desired therapeutic or prophylactic effect, while minimizing untoward or undesirable toxicities or other side effects.

As described herein, an activator site is selected based on its correspondence and/or association with the context in which the two or more protide effectors are to be liberated so as to initiate or potentiate their functions. Therefore, as long as an activator is associated with the context, the invention can be practiced with any context desired. Those skilled in the art will appreciate that, given the versatility of activators useful for practicing the invention as described herein, a protide can be designed based on virtually any context desired, inluding, for example, vascular injury, presence of a neoplasm or cancer, infection, and inflammation.

In one embodiment, the protide is an antimicrobial protide, which also can be referred to as an antimicrotide. Cleavage sites for strategic proteases can be engineered into multifunctional antimicrobial protides so as to represent the activator site of the protide. Upon activation of the protease in the localized or generalized context of tissue injury or infection, as selected by the user, the inactive protide is cleaved, liberating independent and active molecules to effect their respective biological functions. Prior to and beyond the setting of activation of the strategic protease representing the activator, the mosaic protide construct is relatively inactive both with respect to antimicrobial function and host cell toxicity. A mosaic protide construct can consist of an indefinite number (1 through n) of effector and activator domains that can vary in function, activation, position, continuity, or sequence. Effectors corresponding to one or more protides activated by the same or distinct activators also can function synergistically, and/or can recombine in a manner facilitating their complementary functions.

As an example, in the context of vascular injury, a protide activator can be selected that specifically represents this particular context, for example, a clotting cascade protease such as thrombin, or a complement fixing protease such as a C3 convertase, for example, C4B2A or C3bBb. Similarly, as another example, a protide activator can be selected that represents a broader constellation of symptoms or conditions, such as sepsis, in which corresponding activators can include serine proteases associated with systemic inflammation, sepsis, or injury, such as activated protein C.

A further embodiment of the invention encompasses antineoplastic protides, which also are referred to as antineotides. Many tumor cells produce or overexpress characteristic activators, such as matrix metalloproteinases (MMP) or other enzymes that are not expressed by, or at levels much higher than normal cells. Consequently, the activator can be a tumor-specific protease, for example, a matrix metalloproteinase or thymidylate synthase (TS), which is overexpressed in the majority of cancers. A tumor-specific protease also can be associated with a more narrow neoplastic context, such as a serine protease that is specifically expressed in prostate cells, for example, PSA, human kallikrein-2 (hK2), human kallikrein-11 (hK11) and TMPRSS2.

Figure 10:
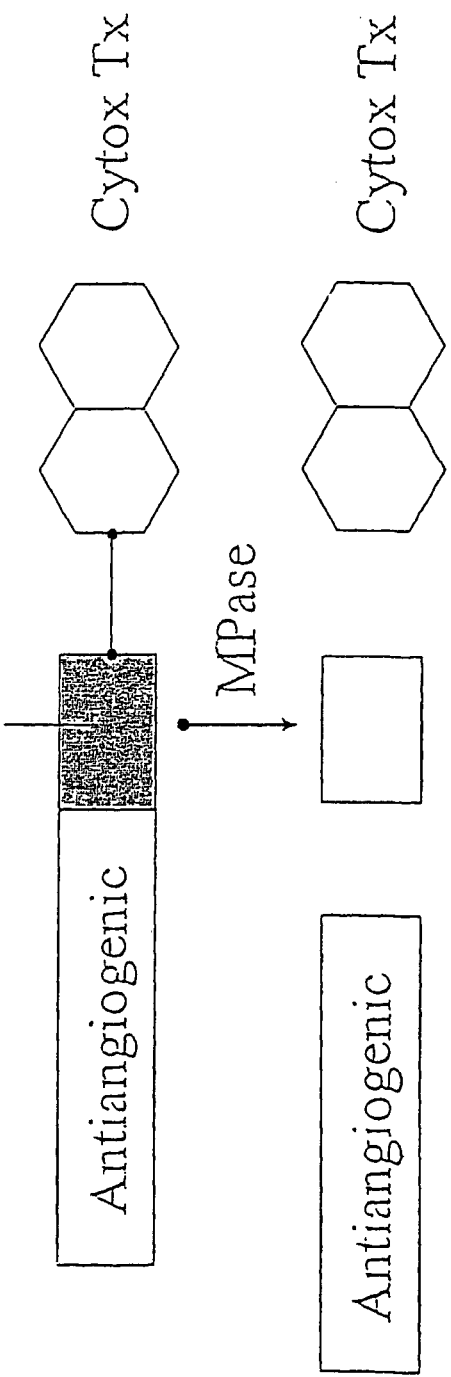
FIG. 10 shows a specific example of an invention antineotide.

In the example shown in FIG. 10, metalloproteinase can serve as an activator that cleaves the mosaic antineotide at the activator site. In this example, one effector domain is an anti-angiogenic peptide that would serve to restrict vascular access to a tumor, the other is a more conventional antineoplastic chemotherapeutic agent. Each domain is liberated in the context of metalloproteinase or other relevant activator as independent molecules to effect their individual and/or complementary antineoplastic functions. Prior to and beyond the local setting of activation, the mosaic construct can be significantly less toxic to normal cells than either individual domain. Thus, context activation at sites of tumor cell activity localizes and activates the antineotide.

In yet another embodiment, the context can be the presence of an inflammatory response as described above, and the effector(s) can be cytokine functional groups, such as those of interleukin-1 or tumor necrosis factor-alpha, or chemotactic cytokines (chemokines) such as interleukin-8, IP-10 or MIG, known to be involved in the coordination, for example, trafficking or navigation, of T-lymphocytes, neutrophils, macrophages, or other immune effector or immunoregulatory cell types to the site of inflammation. The nonapeptide bradykinin is a classic mediator of inflammatory response that is generated from high molecular weight precursors termed kininogens by limited proteolysis mainly in response to tissue injury. Most of the biological actions of bradykinin are mediated through at least two different receptors, the bradykinin B1 and B2 receptors.

The proteins encoded by the serine protease gene family are useful activators in a variety of contexts. Serine proteases are protein-cleaving enzymes that play important roles in normal and pathological physiological processes including protein processing or digestion, for example, trypsin and chymotrypsin; tissue remodeling, for example, stratum corneum chymotryptic enzyme and urokinase; blood coagulation; for example, plasminogen activator and thrombin; fertility, for example, acrosin; inflammatory responses, for example, elastase; tumor cell invasion, for example, uPA3; and programmed cell death, for example, granzymes. Thus, serine proteases are associated with a variety of contexts and can be selected as activators for an invention protide targeted for activation in any of the contexts with which they are associated. It is understood that, depending on the desired application, a specific protide activator site can be any enzyme, including, for example, a lipase, esterase, kinase, endo- and exonuclease.

One example of an activator molecule is a protease expressed by a bacterial pathogen, such as a sortase enzyme expressed by *Staphylococcus aureus* (*S. aureus*). The bacterial pathogen *S. aureus* is increasingly resistant to most conventional antibiotics, including, for example, methicillin and vancomycin, and is associated with increasing mortality and morbidity. *S. aureus* produces several virulence factors that are necessary to achieve and propagate infection, among them sortase, a transpeptidase that is essential for *S. aureus* to attach to its surface molecules that are necessary for binding, immunoavoidance, and virulence, promoting the ability of this organism to cause infection. A protide can be prepared integrating an activator site that is a specifically recognized substrate for sortase as the activator. In the context of an *S. aureus* infection, sortase will naturally be expressed and serve to activate the protide by cleavage of the activator site. Depending on the effectors, which can have for example, distinct antimicrobial and immunomodulatory functions that are activated upon cleavage of the activator site, the bacteria will be killed by the antimicrobial effector, while immune effector cells will be recruited to the site by the immunomodulatory effector. In this example, if the organism responds by compensatory increases in sortase expression, more protides will be activated. Alternatively, if the organism ceases sortase expression, it no longer will be able to attach necessary proteins to its surface and, consequently, will have reduced or no virulence. Moreover, since sortase is present on the extracellular aspect of the organism, protides do not accumulate within the target cell, likely circumventing efflux-mediated resistance. Furthermore, an invention protide can contain distinct effectors that, upon activation, can inhibit one or more sortase type enzymes, and target another essential structure such as the staphylococcal membrane. It is understood that such other enzymes known in the art to mediate virulence in both Gram positive and Gram negative bacteria also are examples of useful activators of protides designed to have a broad antibacterial spectrum. Alternatively, more narrowly defined protides can be designed with activator(s) present only in the context of one or a few specific types of bacteria. Moreover, based on the teachings provided herein, the skilled person can design and prepare analogous protide effector constructs and corresponding activator target sets in other pathogens, including other drug resistant bacterial species, as well as important fungal pathogens such as *Candida albicans*, and viral pathogens such as human hepatitis C virus and HIV.

Thus, activation of a protide of the invention takes place in a context associated with or unique to a specific condition. In addition or as an alternative to inhibiting a target or process directly, a therapeutic strategy highly susceptible to mutation-based resistance, a protide of the invention can be specifically designed to, for example, subvert essential virulence factors or pathogenic mechanisms as a means to diagnose, prevent, or treat, disease. Most conventional antibiotics retard viral, bacterial, fungal, or protozoal proliferation by entering the microbes and interfering with the production of components needed to for homeostasis, metabolism, synthesis, or reproduction, for example, by impairing DNA, RNA, or protein manufacture, or perturbing cell wall or membrane structures. Antibiotic resistance typically involves one or more simple point mutations that slightly change the structure of antibiotic target, for example, the cell wall or ribosomal subunits, such that the antibiotic is no longer effective. Such a slight change in structure with no effect on function is sufficient to inhibit the antibiotic's effect upon the target. Another common reason for rapidly developing resistance against conventional antibiotics is that an enzyme the pathogen naturally produces interferes with the antibiotic such the antibiotic does not reach its target structure in an active form or in sufficient concentration to be efficacious.

An antimicrobial protide of the invention consisting solely of peptide effectors (also referred to an antimicrotide), can include two or more effectors that encompass, for example, an antimicrobial peptide, toxicity-neutralizing peptide, immunomodulatory peptide, ligand-targeting peptide, or any other polypeptide sequence expected to have specific function(s) when activated in the context of microbial infection or host cellular, tissue, organ, or systemic response to tissue injured due to infection. Antimicrobial peptides that exert potent microbicidal action against pathogens, including those that are resistant to conventional antibiotics, are useful as an effector in a protide of the invention. Antimicrobial peptides can be toxic to human or mammalian cells if indiscriminately targeted, or can have suboptimal activities in complex biomatrices such as blood, plasma, or serum due to inactivation or inadequate accumulation at sites of infection. These undesirable properties can be avoided by utilizing antimicrobial peptides as effectors in the invention protides, where they remain relatively inactive until specifically activated either by activators such as the microbial target cells or their components in the context of infection, by activators generated by tissue injured due to infection, or combinations thereof.

Antibiotides illustrate another subset of anti-infective protides and represent useful protides of the invention based on their ability to prevent or treat infection, and/or subvert bacterial drug resistance mechanisms. Rather than inhibiting a bacterial target or process directly as attempted by conventional antibiotics, a therapeutic strategy that is highly susceptible to mutation-based resistance, antibiotides are designed to subvert essential virulence factors or pathogenic mechanisms to prevent or treat disease.

Figure 7:
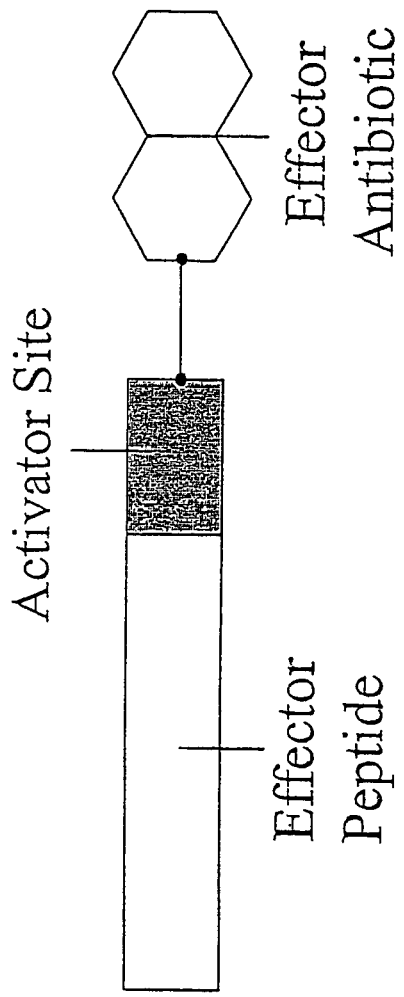
FIG. 7 shows the general conceptual scheme for an invention antibiotide.
Figure 8:
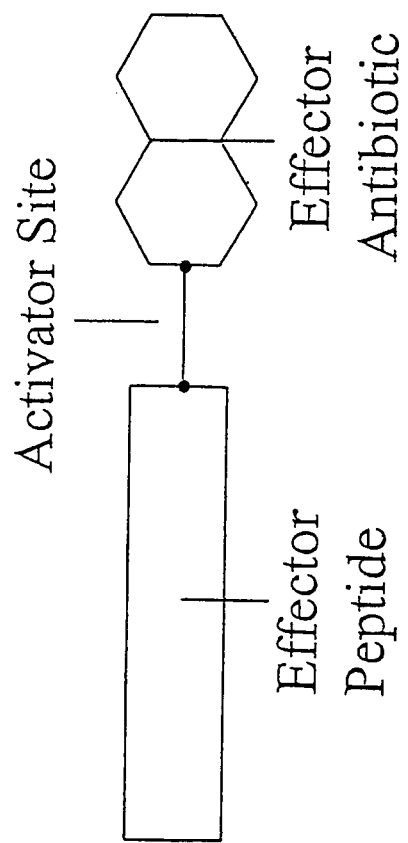
FIG. 8 illustrates a specific example of an invention antibiotide.

FIG. 7 shows the general conceptual scheme for an invention antibiotide. An example of an invention antibiotide consists of an activator site that is cleaved by the activator thrombin, liberating two effectors, the antimicrobial peptide (AP)

and beta-lactam (b-lactam) antibiotic (FIG. 8). Thrombin is a serine-protease produced in the local context of vascular injury or infection. In this context, thrombin is present and cleaves the antibiotide activator site leading to activation of the effectors, the antimicrobial peptide (AP) and beta-lactam antibiotic, which have individual and synergistic antimicrobial functions. In particular, the AP represents a potent microbicidal peptide, while the b-lactam antibiotic exert a distinct, but complementary antimicrobial effect. It is understood that conventional antibiotics other than b-lactam class agents such as, for example, quinolones, anti-metabolites, aminoglycosides, rifampins and rifamycins, tetracyclines, macrolides, azoles, and any other class of therapeutic or prophylactic agent, anti-infective or other, also are useful effectors in an invention antibiotide. Prior to thrombin-activation, the mosaic protide construct is relatively inactive, minimizing or reducing the non-selective toxicity of AP, while the b-lactam is protected from b-lactamase enzymes which can degrade the antibiotic component. Thus, presence of the activator thrombin in the context of vascular infection localizes and activates the prodrug antibiotide. Moreover, activation of a protide containing an effector that increases target cell permeability to another effector such as, for example, to a conventional antibiotic, can significantly augment the efficacy of one or both effector species, or of the combination of such, by allowing increased access to intracellular targets, or circumvent efflux or impermeability resistance mechanisms.

As described herein, context-activated protides offer multiple potential advantages as compared with conventional diagnostic, prophylactic, or therapeutic agents, including sensitivity to an increase in expression of an activator, for example, a microbial virulence factor or hallmark indicator, which results in a corresponding direct increase in protide activation and function. Significantly, context-activated protides can allow for, favor and promote survival of microbial, non-malignant, or other cells that do not express virulence factors or other unfavorable traits, which would otherwise activate protides resulting in injurious or lethal consequences to the activating target cell. Thus, a protide of the invention can be prepared that does not indiscriminately inhibit or kill, for example, normal flora microorganisms, that can often provide additional contributions to host defense and health. As described herein, a protide of the invention has characteristics that can also favor suppression of expression or hyperexpression of virulence factors, which often accompanies treatment with conventional antibiotics of microbial or other target cells, for example, bacteria that hyper-express toxins as they are being killed by classical antibiotics. Thus, use of invention protides avoids the increased expression of toxins that is associated with conventional therapies and that can lead to worsened or accelerated morbidity and mortality. Significantly, a context-activated invention avoids promoting the induction of classical or conventional resistance mechanisms by being designed to target these cells, their resistance mechanisms, or the molecules or pathways that confer these mechanisms as the intended activator(s).

Figure 9:
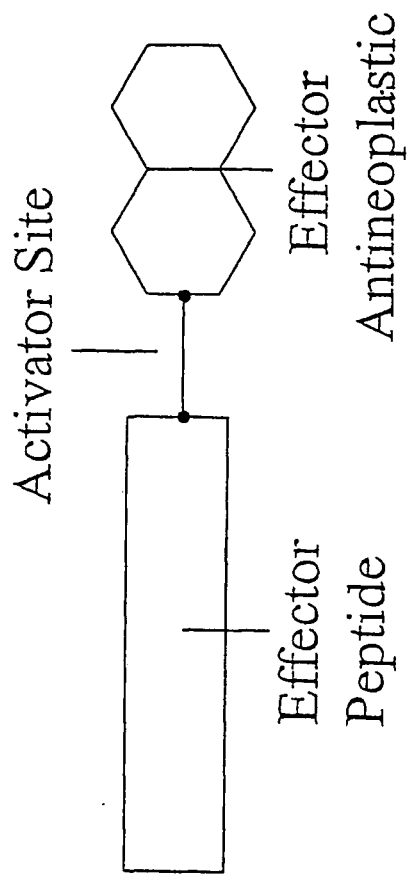
FIG. 9 shows the general conceptual scheme for an invention antineotide.

Antineotides represent a further subset of the invention protides. FIG. 9 shows a general conceptual depiction of an invention antineotide. An invention antineotide can be designed to contain one or more activator sites that are responsive to tumor cell-characteristic activators, such as matrix metalloproteinases, which are enzymes that are either not expressed or expressed at much lower levels in normal cells, allowing these enzymes to be exploited as activators that cleave the mosaic antineotide at the activator site.

It is understood that additional activators generally or specifically corresponding to neoplastic target cells can also be useful components of an antineotide mosaic protide of the invention. For example, an antineotide can be composed of a permeability increasing effector such as a peptide, and an antisense nucleic acid sequence, such that activation of the protide into its peptide and nucleic acid components provides a highly specific and advantageous means of inhibition or killing of the target cell. As a consequence of permeabilization of the target cell by the peptide, sufficient levels of the antisense nucleic acid sequence can enter the cell, hybridize with and block the corresponding complementary strand of nucleic acid, thus inhibiting crucial functions such as DNA replication or mRNA expression, transcription, and/or translation. Thus, an invention protide can be designed that, upon context activation, introduces a nucleic acid into a cell.

In the example of an antineotide mosaic protide shown in FIG. 10; one effector domain is an antiangiogenic peptide, the other is an antineoplastic chemotherapeutic agent. Each domain is liberated in the context of metalloproteinase or other relevant activator as independent molecules to effect their individual and synergistic antineoplastic functions. Moreover, prior to activation, the mosaic construct can be significantly less toxic to normal cells than either individual domain. Thus, context activation at sites of tumor cell activity localizes and activates the antineotide.

Those skilled in the art will appreciate that many variations of the protides exemplified herein can be prepared based on many strategic or favorable permutations encompassing the activator sites as well as on the effectors that are chosen based on the particular context activation and biological functions, respectively, desired by the user. A protide of the invention can consist of two or more effectors having at least two distinct diagnostic or biological functions. The effectors contain or are separated by one or more strategic activator sites. For example, variations, of the above protide example can contain distinct effectors that, upon activation, inhibit one or more sortase enzymes directly, and target another essential structure such as the staphylococcal membrane, or an intracellular target or pathway. In addition to these strategies, protides are designed to be relatively inactive at sites other than their appropriate microenvironmental context such that inadvertent toxicity or activation is minimized. Given the teachings provided herein, it is understood that similar paradigms can be extended to a broad range of potential therapeutic applications for protides of the invention.

Set forth in FIG. 6, are examples of several permutations of effector biological functions and activators useful in preparing an invention protide. Those skilled in the art will appreciate that the combinations set forth herein are only exemplifications of the invention protide concept and that the user can translate the protide concept into any desired combination of effectors and activator sites so as to customize and invention protide having desired biological functions that are activated in a specific context. It is understood that a given protide can be narrow or broad in spectrum, strategically corresponding to the degree to which activator expression is conserved among or unique to potential target cells or tissues. Set forth in FIG. 6(B) are examples of general and specific effectors and activators useful for the preparation of an invention protide.

Figure 11:
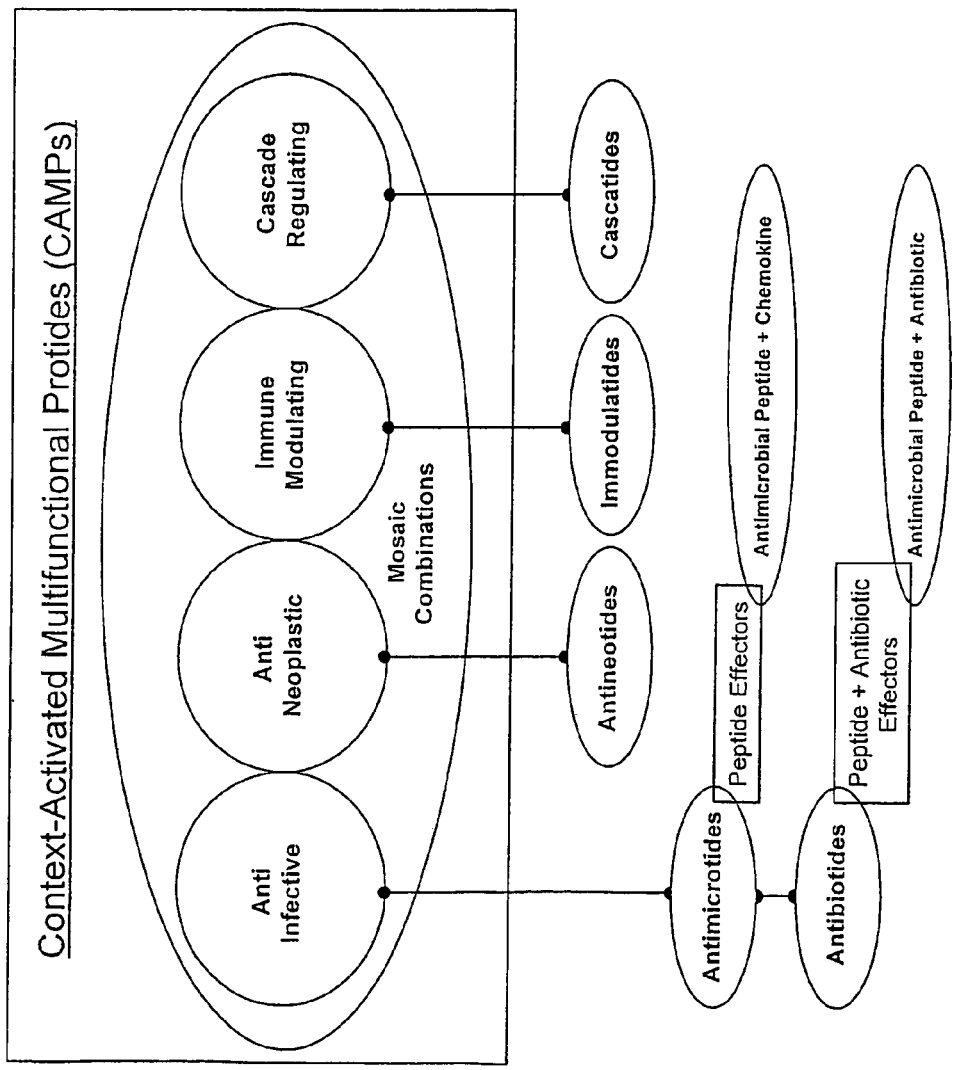
FIG. 11 demonstrates examples of several of the possible mosaic combinations of effectors that can be incorporated into a context-activated multifunctional protide of the invention.

FIG. 11 illustrates examples of both general and specific activators and effectors. As described herein, based on the teachings provided by this invention those skilled in the art will be able to design or customize a protide or combination of protides that encompasses any permutation of the activators and effectors described herein as well as others known in the art. Mosaic combinations of context-activated multifunctional protides can encompass, for example, anti-infective, anti-neoplastic, immune modulating and cascade regulating functions.

A protide of the invention employs at least two effectors individually having distinct biological functions, for example, antimicrobial and immunomodulating; antimicrobial peptide and complementary antibiotic; or enzyme-inhibitor and antimicrobial peptide. Effectors can include polypeptides and non-peptidic molecules, including, for example, conventional antibiotic compounds, antineoplastic compounds, immunomodulatory compounds, apoptotis-inducing compounds, apoptosis-inhibiting compounds, and apoptosis-modulating compounds. Consequently, a protide of the invention can contain combinations or sets of any two or more biological functions, for example, anti-toxic and antimicrobial, anti-neoplastic and anti-angiogenic, antimicrobial and immunomodulatory, or pro-apoptotic and anti-angiogenic.

If desired, a protide of the invention can be designed so as to derive its own context. In particular, an effector, for example, an antimicrobial peptide, can be chosen that seeks out or accumulates in the presence of the target until a critical or threshold concentration is achieved in a localized area. In this regard, antimicrobial or antineoplastic protides can be further specified as to their context for activation. Likewise, strategic or diagnostic protides with imaging-detectable labels are useful to localize the specific area(s) of disease process; in the absence of disease the protides are cleared without rendering a definitive or characteristic signal. In certain embodiments of the invention, an effector also can be selected to self-amplify or self-perpetuate, or to catalyze or modulate endogenous regulatory cascades. As a result, a protide of the invention also can be designed to amplify a process, reaction or cascade that occurs naturally even in the absence of the protide. As described herein, a cascade-regulating protide of the invention, also referred to as cascatide, can promote, suppress, or otherwise modulate biological pathways, for example, signal transduction, coagulation, apoptosis.

As described herein, an effector having an antibiotic biological function can act directly by inhibiting a virulence factor, such as sortase, that acts as an activator, or can act indirectly by targeting another essential structure, for example, the bacterial membrane.

An effector with an immunomudulatory function can consist of an immunomodulatory molecule that, upon activation of the effector, mediates an immune response that is specific for a target antigen or mechanism of pathogenesis, or it can be nonspecific. A specific immunomodulatory molecule alters an immune response to a particular target antigen. Examples of specific immunomodulatory molecules include monoclonal antibodies, including native monoclonal antibodies, drug-, toxin- or radioactive compound-conjugated monoclonal antibodies, and antibody-dependent cell cytotoxicity-(ADCC) or phagocytosis-targeting (eg., opsonizing) molecules. Such immunomodulatory molecules stimulate an immune response by binding to antigens and targeting opsonized cells for inactivation or destruction. An effector with an immunomudulatory function can consist of an immunomodulatory molecule to suppress an immune response to an antigen. For example, a toleragenizing molecule can be used to suppress an immune response to a self-antigen.

An effector with an immunomodulatory function also can consist of a non-specific immunomodulatory molecule that can stimulate or inhibit the immune system in a general manner through various mechanisms that can include, for example, stimulating or suppressing cellular activities of immune system cells. Nonspecific immunomodulatory molecules useful for stimulating an immune responses include, for example, agents that stimulate immune cell proliferation, and/or immune cell activation and production of cytokines and co-stimulatory molecules. Well known immunomodulatory molecules that modulate immune response are, for example, interleukins, interferons, levamisole and keyhole limpet hemocyanin. Nonspecific immunomodulatory molecules useful for suppressing immune responses include, for example, agents that inhibit cytokine synthesis or processing, specific cytokine receptor blocking reagents such as soluble receptors and receptor antagonists, and cytokines that downregulate or inhibit the production of other immunomodulatory molecules. Well known immunomodulatory molecules for suppressing an immune response include, for example, cyclosporin, rapamycin, tacrolimus, azathioprine, cyclophosphamide and methotrexate. Immunomodulatory molecules can be contained in a mixture of molecules, including a natural or man-made composition of molecules. Exemplary natural compositions of immunomodulatory compounds include, for example, those contained in an organism such as Bacille Calmette-Guerin or *Corynbacterium parvum*. Exemplary man-made immunomodulatory compositions of molecules include, for example, QS-21, DETOX and incomplete Freund's adjuvant.

As described above, the biological function of an effector that corresponds to an invention protide can be antimicrobial. An effector with an antimicrobial biological function can consist of an antimicrobial molecule that, upon activation of the effector, mediates an antimicrobial response.

Antimicrobial peptides generally are broad spectrum antimicrobial agents that can be useful as effectors in an invention protide. These peptides, which are useful as effectors in certain invention protides, typically disrupt microbial cell membranes and other essential processes or targets, leading to eventual cell death that may or may not involve cell lysis. Over 500 antimicrobial peptides occur naturally. In addition, analogs have been synthesized de novo as described in Javadpour et al., *J. Med. Chem.* 39:3107-3113 (1996); and Blondelle and Houghten, *Biochem.* 31: 12688-12694 (1992), each of which is incorporated herein by reference. A special group of membrane interacting antibiotics are pore forming peptides like alamethicin, gramicidin A, and melittin, which kill cells by perforating the electrochemical gradients of membranes and depleting their energy storage. While some antimicrobial peptides such as melittin are non- or poorly selective and damage normal mammalian cells at the minimum microbicidal concentration, others are more selectively toxic for specific microbial pathogens, such as bacterial cells. For example, the naturally occurring magainins and cecropins exhibit substantial bactericidal activity at concentrations that are not typically lethal to normal mammalian cells. These and other known antimicrobial peptides can be useful as effectors in an invention protide.

An antimicrobial peptide useful as an effector in an invention protide frequently contains cationic amino acids, which are attracted to the head groups of anionic phospholipids, leading to the preferential disruption of negatively charged membranes. Once electrostatically bound, the amphipathic helices can distort the lipid matrix, resulting in loss of membrane barrier function (Epand, *The Amphipathic Helix*, CRC Press: Boca Raton (1993); Lugtenberg and van Alphen, *Biochim. Biophys. Acta* 737:51-115 (1983), each of which is incorporated herein by reference). Prokaryotic cytoplasmic membranes maintain large transmembrane potentials and have a high content of anionic phospholipids. In contrast, the outer leaflet of eukaryotic plasma membranes generally has low membrane potential and is almost exclusively composed of zwitterionic phospholipids. Thus, due to such distinctions in membrane compositions and/or energetics, antimicrobial peptides can preferentially disrupt prokaryotic membranes as compared to eukaryotic membranes and are useful as effectors in a protide of the invention.

An effector having antimicrobial biological function that is initiated or amplified upon activation can consist of a naturally occurring or synthetic peptide having antimicrobial activity, which is the ability to kill or slow the growth of one or more microbes. An antimicrobial effector can, for example, kill or slow the growth of one or more strains of bacteria including a Gram-positive or Gram-negative bacteria, as well as fungi or protozoa. Thus, an antimicrobial effector can have, for example, bacteriostatic or bacteriocidal activity against, for example, one or more strains of *Escherichia coli*, *Pseudomonas aeruginosa* or *Staphylococcus aureus*. While not wishing to be bound by the following, an antimicrobial effector can have biological activity due to the ability to form ion channels through membrane bilayers as a consequence of self-aggregation.

An antimicrobial peptide useful as an effector in an invention protide is typically basic and can have a linear or cyclic structure. As discussed further below, an antimicrobial peptide can have an amphipathic alpha-helical structure (see U.S. Pat. No. 5,789,542; Javadpour et al., supra, 1996; Blondelle and Houghten, supra, 1992). An antimicrobial peptide useful as an effector in an invention protide also can be, for example, a beta-strand/sheet-forming peptide as described in Mancheno et al., *J. Peptide Res.* 51:142-148 (1998).

An antimicrobial peptide useful as an effector in an invention protide can be a naturally occurring or synthetic peptide. Naturally occurring antimicrobial peptides have been isolated from biological sources such as bacteria, insects, amphibians and mammals and are thought to represent inducible defense proteins that can protect the host organism from bacterial infection. Naturally occurring antimicrobial peptides include the gramicidins, magainins, cryptdins, defensins and cecropins (see, for example, Maloy and Kari, *Biopolymers* 37:105-122 (1995); Alvarez-Bravo et al., *Biochem. J.* 302:535-538 (1994); Bessalle et al., *FEBS* 274:151-155 (1990); and Blondelle and Houghten in Bristol (Ed.), *Annual Reports in Medicinal Chemistry* pages 159-168 Academic Press, San Diego, each of which is herein incorporated by reference). An antimicrobial peptide also can be an analog of a natural peptide, especially one that retains or enhances antimicrobial potency or selectivity.

An antimicrobial peptide incorporated within a protide of the invention can have low mammalian cell toxicity as can readily be determined via routine assays. For example, mammalian cell toxicity can be estimated by lysis of human erythrocytes in vitro as described in Javadpour et al., supra, 1996. An antimicrobial peptide having low mammalian cell toxicity can be less lytic to human erythrocytes, or require concentrations significantly exceeding those required for antimicrobial activity, as compared with highly toxic peptides. It is understood, that an antimicrobial peptide incorporated within a protide of the invention also can have considerable mammalian cell toxicity that can be modulated by the context activation.

A microbe is a minute life form that can include, for example, both prokaryotic and eukaryotic organisms, as well unicellular and multicellular organisms. Bacteria are a specific example of unicellular, prokaryotic microbes whereas protozoa such as amoebas, ciliates, flagellates, and sporozoans are specific examples of unicellular eukaryotic microorganisms. Examples of multicellular eukaryotic microorganisms include, for example, multiceluar fungi such as molds. Microbes can vary in many ways, such as morphology, virulence factor expression, composition and structure, oxygen and nutritional requirements, motility, susceptibility or resistance to antimicrobial agents, and many other aspects.

As described above, the biological function of an effector incorporated within a protide of the invention can also be antineoplastic or tumoricidal, terms used interchangeably herein. Furthermore, the biological function of an effector incorporated within a protide of the invention can be pro- or anti-apoptotic. In addition, the biological function of an effector incorporated within a protide of the invention can be pro- or anti-angiogenic.

A neoplastic cell is a cell that proliferates without normal homeostatic growth control resulting in a benign or malignant lesion of proliferating cells. Such a lesion can be located, for example, in the gastrointestinal system, such as in the colon, small intestine, stomach, appendix and rectum. Cancer describes a class of diseases characterized by the uncontrolled growth of aberrant cells, including all known cancers, and neoplastic conditions, whether characterized as malignant, benign, hematologic, soft tissue or solid tumor. Specific cancers include digestive and gastrointestinal cancers, such as anal cancer, bile duct cancer, gastrointestinal carcinoid tumor, colon cancer, esophageal cancer, gallbladder cancer, liver cancer, pancreatic cancer, rectal cancer, appendix cancer, small intestine cancer and stomach (gastric) cancer. Neoplastic cells associated with either benign or malignant tumors are associated with particular biomarkers that can be exploited as activators of an invention protide designed to be activated in the particular context of the tumor.

One of the hallmarks of cancer as well as that of over seventy other diseases, including diabetic blindness, age-related macular degeneration, rheumatoid arthritis and psoriasis, is the body's loss of control over angiogenesis. Angiogenesis-dependent diseases result when new blood vessels either grow excessively or insufficiently. Excessive angiogenesis occurs when diseased cells produce and release abnormal amounts of angiogenic growth factors, overwhelming the effects of natural angiogenesis inhibitors. The resulting new blood vessels feed diseased tissues, which in turn destroy normal tissues. Therefore, a biological function of an effector incorporated within a protide of the invention can be anti-angiogenic.

Upon their release, angiogenic growth factors diffuse into nearby tissues and bind to specific receptors located on the endothelial cells of nearby preexisting blood vessels. Once growth factors bind to their receptors, the endothelial cells become activated and send signals from the cell surface to the nucleus. As a result, the endothelial cell's machinery begins to produce new molecules including enzymes that create tiny holes in the basement membrane that surrounds existing blood vessels. As the endothelial cells begin to proliferate, they migrate out through the enzyme-created holes of the existing blood vessel towards the diseased tissue; in the case of cancer, the endothelial cells migrate towards the tumor. Specialized molecules called adhesion molecules, such as selectins or integrins, provide anchors that allow the new blood vessel to sprout forward. Additional enzymes, among them matrix metalloproteinases (MMPs), are produced to dissolve the tissue in front of the growing blood vessel tip to allow for its continued tissue invasion. As the vessel extends, the tissue is remolded around the vessel and endothelial cells roll up to form a new blood vessel. Subsequently, individual blood vessels, connect to form blood vessel loops that can circulate blood. Finally, the newly formed blood vessels are stabilized by specialized muscle cells (smooth muscle cells, pericytes) that provide structural support and blood flow through the neovascularized tissue begins. As those skilled in the art will appreciate, the enzymes described above as well as other art-known enzymes associated with the progression of angiogenesis are useful as activators associated with the context of angiogenesis.

Significantly, angiogenesis is one of the critical events required for cancer metastasis. Metastasis, the ability of cancer cells to penetrate into lymphatic and blood vessels, circulate through the bloodstream, and invade and grow in normal tissues elsewhere makes cancer a life-threatening disease. Tumor angiogenesis is the proliferation of a network of blood vessels that penetrates into cancerous growths, supplying nutrients and oxygen and removing waste products.

Therefore, the invention protides and related methods are characterized, in part, by their multifunctionality and context-specifity desired. Those skilled in the art will appreciate that, given the versatility of effectors and activators useful for practicing the invention as described herein, a protide can be designed to initiate any two or more biological functions in virtually any context desired.

Figure 4:
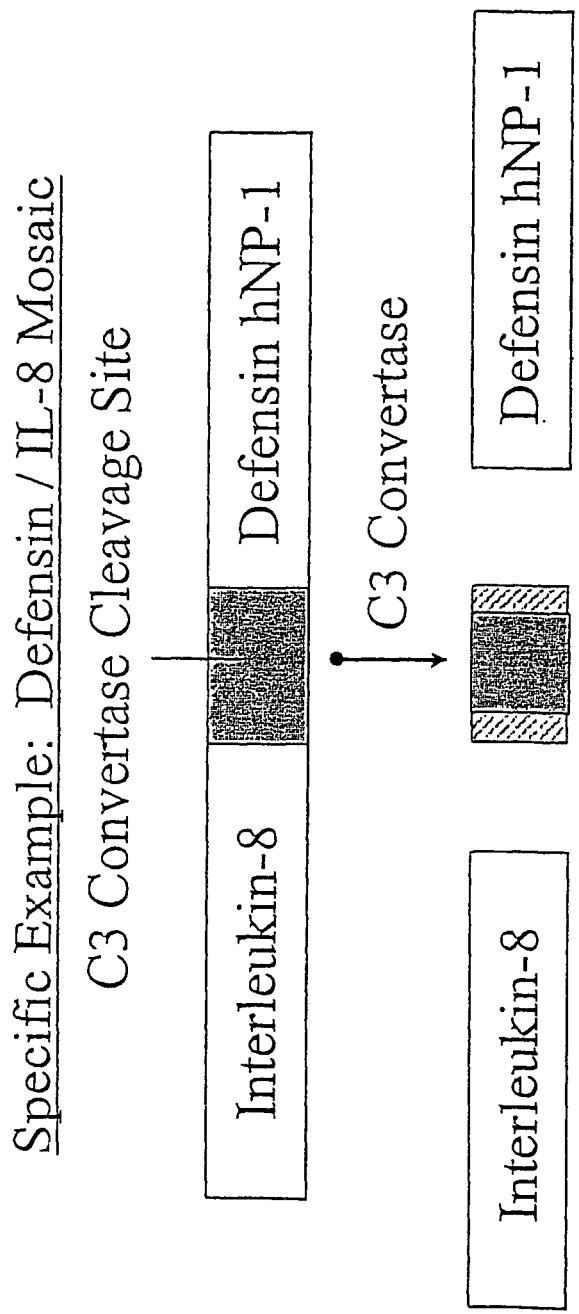
FIG. 4 shows a further specific exemplification of an invention protide that is activated in the context of complement fixation by C3 convertase serine protease activators that cleave the mosaic protide at the cleavage site, liberating the effector domains IL-8 and defensin hNP-1 as independent molecules to effect their respective functions.
Figure 5:
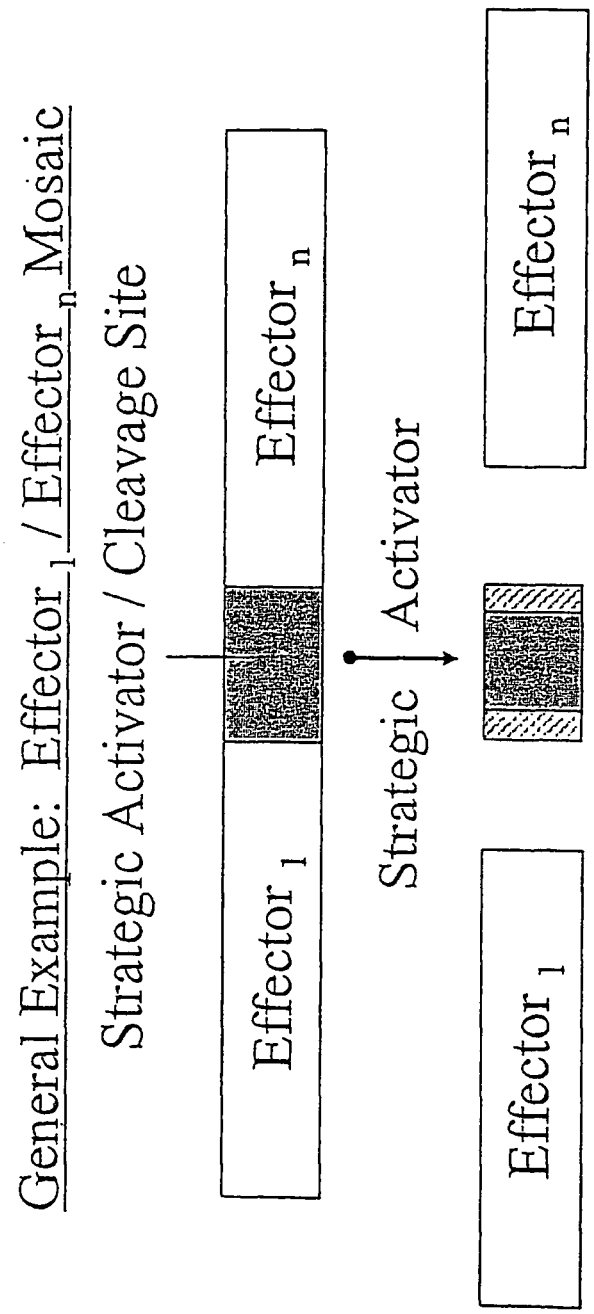
FIG. 5 shows a general example of an invention protide that is activated by a strategic protease activator in the context of inflammatory responses to tissue injury or infection trigger activation of otherwise inactive proteases.

In a further embodiment, the invention provides a method of treating infection by administering to a subject a therapeutically effective amount of the context-activated protide. The protide, also provided by the invention, can have one activator site and two effector peptides having distinct biological functions, wherein the distinct biological functions are antimicrobial and immunomodulatory. One of the effector peptides in this embodiment can be interleukin-8, the other effector peptide can be defensin hNP-1, and the activator can be a protease such as a clotting cascade protease or a complement fixing protease as described herein. As shown in FIG. 4, antibody recognition of a microbial pathogen, or the pathogen itself, can trigger classical or alternative complement cascades (respectively), resulting in relatively local production of C3 convertase serine proteases, either C4b2a or C3bBb. Each of these C3 convertase enzymes can serve as a protide activator in this embodiment, cleaving the mosaic protide at the cleavage site, liberating the effector domains IL-8 and defensin hNP-1 as independent molecules to effect their respective functions as described above. Prior to and beyond the setting of activation in the context of the complement cascade, the mosaic construct remains charge-neutralized and relatively inactive, minimizing the non-selective toxicity of hNP-1, and the indiscriminant stimulating effects of IL-8. Thus, complement fixation specifically upon pathogenic microorganisms and/or at sites of infection is the context that localizes and activates the protide.

Figure 3:
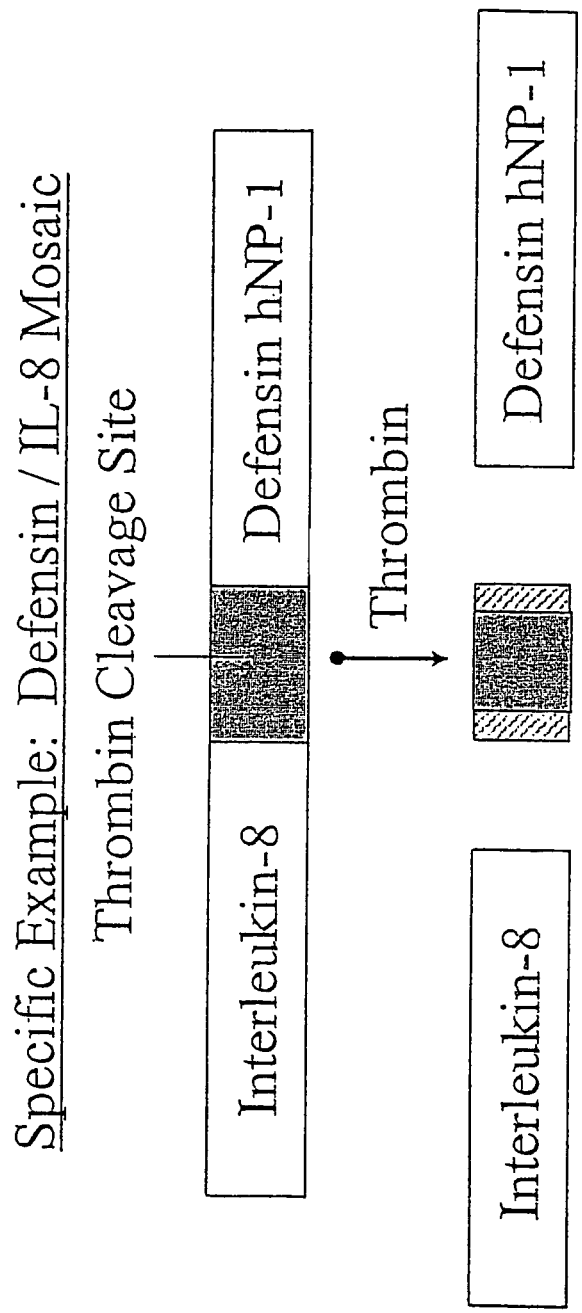
FIG. 3 shows a specific example of an invention protide that is activated in the context of vascular injury or infection.

In the specific embodiment depicted in FIG. 3, thrombin is the protide activator that cleaves the mosaic protide at the cleavage site resulting in the liberation of the effector IL-8 and defensin hNP-1 antimicrobial peptide domains into independent molecules to effect their respective functions of unfavorable cytotoxic effects against host cells (hNP-1) and recruitment and stimulation of neutrophils to respond specifically to the sites of infection (IL-8). Prior to thrombin-activation, the mosaic construct is designed to be charge-neutralized and relatively inactive, minimizing the non-selective toxicity of hNP-1, and the indiscriminant inflammation stimulating effects of IL-8. Thus, thrombin activation at sites of vascular injury or infection itself localizes and activates the protide.

In a further embodiment, the invention provides a method of treating a neoplastic condition by administering to a subject a therapeutically effective amount of a of the invention, for example, a protide encompassing one activator site and two effector peptides having distinct biological functions, wherein the distinct biological functions can include anti-neoplastic, pro-apoptotic, and anti-angiogenic effectors. In a related embodiment, the invention provides a method of treating a condition associated with decreased cell death by administering to a subject a therapeutically effective amount of a protide of the invention that has effectors with apoptotic and anti-angiogenic biological functions.

In a further embodiment, the invention provides a method of treating a microbial infection by administering to a subject a therapeutically effective amount of an antimicrobial protide of the invention containing solely peptide effectors, also referred to an antimicrotide. The protide administered in this embodiment of the invention can include two or more effectors that encompass, for example, an antimicrobial peptide, toxicity-neutralizing peptide, immunomodulatory peptide, ligand-targeting peptide, or any other polypeptide sequence expected to have a specific function when activated in the context of microbial infection or tissue injured due to infection.

In one embodiment, the invention provides a method of treating a microbial infection by administering to a subject a therapeutically effective amount of a hybrid protide of the invention, also termed an antibiotide. A protide can be introduced locally, regionally, or systemically to treat an established infection, or a pathological condition for which presumptive diagnosis indicates empiric therapy that is consistent with eradicating or preventing the progression of an emerging or established infection. An activator of an invention protide useful for treatment of a microbial infection can be associated with either the microbe, for example, a microbial virulence factor or the host organism, for example, a soluble response molecule or protein, or a cell-associated compound.

An invention protide useful for treatment of a microbial infection can be activated by a microbial virulence factor, exoenzyme or other secreted product, surface component, unique metabolic process or pathway, target, or condition of the pathogen. Alternatively, a protide can be activated by host responses to the pathogen. Examples of such activators include, for example, soluble components such as tissue factor, thrombin, complement proteins, fragments of complement activation, coagulation cascade components or reactants, clot dissolution components or reactants, and/or activated protein C or related agents. Also contemplated as activators useful for practicing the invention are, cell-associated activators, for example, platelet, leukocyte, or lymphocyte products including surface-bound or released proteins, enzymes or other reactants.

In applications of the invention method involving an established infection or a host response to infection, activators can be present or generated. An activator useful for activation of a protide of the invention can be advantageously selected based on a high concentration in the immediate proximity of the infection locus so as to allow for activation of the majority of protides in the desired context. One skilled in the art will be able to select an activator that represents the desired activation context. For applications of the invention methods in the arena of microbial infection, context-activation can be designed to specifically occur in the local context of infection so as to effect optimal relative protide effector concentrations in specific contexts of infection. In addition to context activation that maximizes efficacy, the protides and methods of the invention also minimize the potential for inadvertent host cytotoxicity in areas that do not represent the context. Therefore, in the absence of infection, the protide activators are either absent or are present at concentrations insufficient for effective protide activation, thereby minimizing inadvertent or indiscriminant acute toxicity.

In addition to specific pathogen or host molecules that can serve as activators as described above, protides can also be designed to become activated to diagnose, prevent, or treat infection in unique and/or specific biochemical or physiological contexts associated with microbial pathogens. Examples of such biochemical or environmental contexts include ionic, osmotic, pH, oxidation/reduction, or other conditions that are unique to, characteristic of, or present in the context of infection or disease processes that occur upon infection, or host responses to these events. For example, a protide can be designed to require the influence of protonation, conformation change, or other modification that occurs uniquely or disproportionately in the context of acidic pH, to activate the protide or its ensuing effectors by altering their structure-activity relationship(s) from inactive to active. As one example, genitourinary tissues, such as renal tissues or genitourinary mucosa, can exhibit pH values that are decreased normally, or in the setting of infection. A protide designed to be activated only under such acidic conditions could be designed to either be vulnerable to activation in these conditions, or directly activated by these conditions, and thus would be predicted to be active only in such contexts. Alternatively, protides can be designed to be inactive in particular contexts or conditions, such as conditions of relatively high osmotic strength or relatively high pH, so as to minimize or prevent untoward or toxic effects such as nephro- or hepato-toxicity. By way of a further example, activation as well as leukocyte accumulation are conditions associated with infection. Moreover, a fundamental strategy of host defense phagocytes is to phagocytize the microbial pathogen, subjecting it to the harsh environment of the acidic phagolysosome. The compartment so created can become acidified to pH values of 5.5 or lower as the leukocyte responds to the pathogen. Therefore, a protide can be designed that is activated or has amplified or antimicrobial activities, for example, by pH, phagolysosomal enzymes or reactants, or a combination of these conditions, or can amplify or potentiate the antimicrobial mechanisms of leukocytes or other host cells within such settings, so as to inhibit or kill pathogens that enter such cells.

Protide activation also can include conformational, oxidation or reduction-mediated changes in disulfide array, assembly into multimers of two or more homomeric (identical) or heteromeric (non-identical) effectors, or other modifications of the protide and/or its subsequent effectors. In a particular embodiment, protide activation is triggered as a result of protide accumulation, or its resulting effector components, so as to achieve or surpass threshold concentrations required to optimize or catalyze activation or activity through multimerization or other modification in structure or function of the protide or its effectors.

It is understood, that activation can involve combinations of the protide activation strategies described above. For example, a protide can be designed that is not responsive to an activator unless both the protide and the activator are present within a context associated with or resulting from infection or other disease.

Briefly, once a pathogen establishes infection and expresses requisite virulence factor or other activators a protide of the invention can be introduced that contains two functional effectors, for example, one effector that has direct activity against the pathogen and becomes amplified under specific conditions and a second effector that has a chemokine-like motifs or functions. Upon protide activation in the presence of the virulence factor activator in the context of infection the effector binds to and exerts activities against the pathogen that are relatively modest and not toxic to the host. In addition, activation by the microbial virulence factor or in the greater context of infection or disease results in diffusion away from the nidus of infection by the chemokine motif-containing effector, thereby creating a chemotactic gradient that results in influx of immunocompetent cells, for example, leukocytes. The chemokine motif-containing effector thus recruits leukocytes to the site of infection where pathogens exposed to the antimicrobial effector are phagocytosed by the arriving leukocytes, and enter the acidic phagolysosome. The antimicrobial effector exerts amplified activity against the pathogen in the context of the acidic phagolysosome. In this embodiment, the antimicrobial effector functions along with the intrinsic antimicrobial mechanisms within the acidic context of the leukocyte phagolysosome, leading to destruction and clearance of the pathogen. The infection is resolved and the protide was at no point activated beyond the context of infection, Since the antimicrobial effector exerts suboptimal activity under neutral or alkaline conditions of pH, toxicity to host cells and tissues is minimal. Alternatively, protides can be designed to prevent leukocyte activation or accumulation in specific contexts where desirable, yielding for example an anti-inflammatory effect.

An activator can be selected based on the context desired for activation. As an example, nearly all bacterial pathogens integrate peptidoglycan into their cell wall complex. Specific enzymes, including carboxypeptidases and transpeptidases, are necessary to activate and crosslink peptidoglycan precursors to achieve the native matrix. An antimcrobial protide of the invention can therefore be designed to contain activator sites responsive to such activator enzymes that initiate or amplify an antimicrobial effector, as well as collateral inhibition of specific enzymes required for peptidoglycan synthesis. An enzyme that is unique to a targeted context, for example, a peptidoglycan synthesis enzyme, which is unique to bacterial pathogens, is particularly useful as it can be activated in the particular local context of bacterial infection, thereby minimizing inadvertent host cell toxicity. Those skilled in the art will be able to select other activator enzymes that are specific to a desired context for protide activation.

An antimicrobial protide of the invention can therefore be designed such that is activated in a broad context, for example, by selecting an activator that is common to a variety of pathogens or a variety of cancers. Alternatively, a more narrow context can be selected by preparing a protide that encompasses one or more activator sites that are triggered by activators particular to such a narrower context. If desired, a protide of the invention can be designed so as to be activated in the context of Gram-positive versus Gram-negative bacteria. Gram-positive bacteria utilize so-called LPXTG (Leucine-Proline-X-Threonine-Glycine) (SEQ ID NO: 5) or related motifs in structural proteins intended for cell wall or extracellular membrane surface localization. Numerous surface proteins integral for virulence of Gram-positive pathogens such as *S. aureus* and *S. pyogenes* are anchored to the Gram-positive cell wall/envelope complex via a protein processing mechanism, utilizing a C-terminal sorting sequence with an LPXTG (SEQ ID NO: 5) motif. Sortase enzymes are membrane proteins common to many Gram-positive and Gram-negative pathogens that cleave precursor proteins intended for the cell wall/envelope complex between threonine and glycine residues found within the LPXTG (SEQ ID NO: 5) motif. Thus, as an example, a given sortase can catalyze the formation of a covalent amide bond between the carboxyl-sidegroup of threonine and amino-sidegroup of adjacent peptidoglycan. Significantly, the sortase mechanism is predominant in several Gram-positive pathogens including *S. aureus* and *S. epidermidis*, streptococci such as *S. pyogenes, S. pneumoniae*, and *S. agalactiae*, enterococci such as

*E. faecium* and *E. faecalis*, as well as difficult Gram-negative pathogens such as *Ps. aeruginosa* and various members of the family Enterobacteriaceae, where it is integral for maturation of surface protein attachment to the cell wall/envelope complex. Protides can therefore be prepared that contain LPXTG (SEQ ID NO: 5) activation sites that allow exploitation of the sortase mechanism to liberate one or more antimicrobial effectors, leading to competitive inhibition of sortase, which can also be outcompeted by the activator sites from acting on natural substrates to catalyze essential surface protein anchoring.

A further application of an invention protide with antimicrobial biological function is in a species-specific context. Individual species or specific strains of microbial pathogens account for a large proportion of infections including infections due to strains that elaborate penicillinase or cephalosporinase enzymes such as *S. aureus* or *Pseudomonas aeruginosa* (*P. aeruginosa*); pathogens that express high levels of one or more exoenzymes that are believed crucial to virulence such as coagulase of *S. aureus*; a variety of serine proteases elaborated by Gram-negative pathogens such as DegS or DegQ in *Escherichia coli* and AlgW or MucD in *P. aeruginosa*; and phospholipases or aspartyl proteases of the yeast *Candida albicans* (*C. albicans*). Each of the aforementioned virulence factors provides an example of an activator that corresponds to an activator site of an invention protide. Thus, an invention protide can be prepared to be activated by, for example, one or more virulence factors, enzymes, or specific targets of a microbial pathogen as well as any combination thereof. For example, a protide containing D-ala/D-ala motif within its activator site can be designed to mimic a peptidoglycan precursor, such that it becomes activated by peptidoglycan enzymes, thereby liberating antimicrobial peptides in close proximity to the vulnerable cell membrane of the pathogen. Alternatively, examples of protides can also be envisioned in which the activator sites are specific substrates for one or more exoenzymes or other virulence factors required for infection by a pathogen.

In a further embodiment, the invention provides a method of preventing the establishment of infection or onset of symptoms due to the presence of the pathogen in normal individuals, or those at increased risk of infection for any reason. Settings or conditions associated with increased of infection that are appropriate for practicing the invention methods for prophylactic use of protides include, for example, acute or chronic immunosuppression associated with organ transplantation; chronic steroids use in allergy, autoimmune, rheumatoid, or other pathological conditions; diabetes or other pathological conditions attributed to reduced immune functions; cancer; cancer chemotherapy; individuals requiring long-term vascular access, such as those undergoing kidney dialysis or that need ongoing vascular catheterization; infection resulting in an immunocompromised state such as HIV; pre- or post-surgical procedures, or other settings or pathological conditions known to those skilled in the art. In such settings, a protide can be used as a prospective prophylactic agent or pre-antibiotic to protect against pathogens should they colonize and elaborate virulence factor or host response activators directly or indirectly, or that modify a physiological context such that a protide is activated. For example, a protide can be administered to a patient at risk of infection, but not activated unless the pathogens are or become present and virulent, for example, expressing virulence factor activators, or become opportunistic via an increase in pathogen quantity via proliferation, or their upregulation of virulence factor expression to cause overt infection. Absent these conditions, the protide remains inactive and relatively harmless to the host.

Similarly, the context in which an antineotide is activated can be chosen by the user designing the protide. If a broad context is desired for actication, for example, in the context of any tumor cell type, an activator can be chosen that ubiquitous to tumor cells, for example, a metalloproteinase. Alternatively, if activation in a more narrow context is desired, an activator can be selected that represents a particular organ or cell type, for example, Prostate Specific Antigen (PSA) or TMPRSS2, which are serine proteases that are overexpressed in a majority of prostate cancer patients. PSA has been shown to directly degrade extracellular matrix glycoproteins such that any of the degraded products also are localized in the context of a protate neoplastic condition and also can be useful as context-specific activators for an invention protide.

An individual undergoing cancer chemotherapy has a significantly increased risk of infection and represents an example of an appropriate target for prophylactic application of the invention protides and methods. A protide can be introduced prior to and throughout the period of time during which immune suppression is acute as a result of chemotherapy. For example, it is known that a time of great risk for infection often flanks the pre- and post-nidus leukocyte count interval (eg., neutropenia). Hallmark pathogens often associated with such contexts include fungal pathogens that are very difficult to treat once infection has been established such as, for example, *Candida, Aspergillus* and *Mucor*, as well as bacterial pathogens that can overwhelm an immunocompromised host such as, for example, *Staphylococcus, Pseudomonas* and *Enterobacteriaceae*. Given the teachings provided herein, the skilled person will appreciate that protides or appropriate combinations of protides can be specifically used as prophylactic agents against pathogens common to a respective risk of infection. As described above, unless activated, the protide in its inactive form would be essentially inert or exert reduced activity or cytotoxicity, and cleared from the system with little or no adverse effect. However, should the individual become colonized with or infected by a relevant pathogen, the protide(s) becomes exposed to activators, either from the organism or from host responses to the organism such as the organisms virulence factor or exoenzyme, or a host-generated factor that is specific to the desired context because of tissue damage or other effects of infection. In such a prophylactic environment, the effector's biological function(s) that combat the organism can be initiated prior to or at the earliest point in the establishment of infection and can be locally concentrated to the specific context in which activators are present in sufficient quantity or quality, and/or in a milieu consistent with activation.

In a further embodiment, the present invention provides protides and related methods for reconstituting normal homeostasis in individuals with deficiencies in genes or gene products. For example, a protide of the invention can be prepared to be activated in the absence of a protein or other factor associated with normal function. In this embodiment, a protide can be designed that, if exposed to an abnormal condition caused by, for example, the absence of a particular protein, it is subject to degradation by an activator, yielding the deficient protein as an effector, thereby reconstituting the normal condition. Such a protide can be used to reconstitute normal homeostasis in individuals having inherited or acquired defects or deficiencies in one or more gene products.

In a further embodiment, a protide can be prepared that is activated only in the presence of a microorganism, tumor cell, other pathogenic cell, or a component, exoproduct, or metabolite of such, so that the effectors are detectable directly or indirectly for diagnostic purposes. In such a diagnostic embodiment, an effector can be appropriately chosen to allow for easy detection through, for example, calorimetric, immunologic, electronic, radiographic, biochemical or other technique known to those skilled in the art. Thus, in a diagnostic application of the invention protides and methods, specific protides can be prepared that detect and/or diagnose a specific disease or pathogenic state, or their etiologies.

As described herein, an invention protide can have a cascade regulating function (FIG. 11). As described herein, such a protide also referred to as cascatide can be designed to amplify or inhibit an endogenous cascade, for example, a signal transduction cascade or coagulation cascade. In a further embodiment related to cascade-regulating protides or cascatides, the invention provides both pro-apoptotic and anti-apoptotic protides. In particular, a protide can be designed and prepared with one or more activator sites that are specific substrates for one or more specific caspase enzymes, which are expressed when the process of apoptosis is initiated and serve as activators. In this embodiment, the protide is activated to liberate its effector(s) only when apoptosis is activated, at which time the released effector(s) target mitochondria, for example, by means of specific sequence, structure, or composition of the effector, and either amplify the initial apoptotic signal or inhibit the response. If desired, an effector can also be an inhibitor or activator of a particular caspase. A pro-apoptotic cascatide can be useful in applications directed at reducing the severity of a condition associated with a reduction or deceleration in cell, for example, cancer. An anti-apoptotic cascatide can be useful in applications directed at reducing the severity of a condition associated with increased cell death, for example, in the treatment of an ischemic condition, neurodegenerative condition, autoimmune condition, or in anti-aging therapy.

A protide of the invention useful for practicing the methods of the invention can be formulated and administered by those skilled in the art in a manner and in an amount appropriate for the pathological condition to be treated, for example, an infection, neoplastic disorder, inflammation; the rate or amount of inflammation; the weight, gender, age and health of the individual; the biochemical nature, bioactivity, bioavailability and side effects of the particular compound; and in a manner compatible with concurrent treatment regimens. An appropriate amount and formulation for decreasing the severity of a pathological condition in humans can be extrapolated from credible animal models known in the art of the particular disorder. It is understood, that the dosage of a therapeutic substance has to be adjusted based on the binding affinity of the substance, such that a lower dose of a substance exhibiting significantly higher binding affinity can be administered compared to the dosage necessary for a substance with lower binding affinity. For an invention protide several factors can be taken into account when determining the proper dosage, for example, the nature of the protide effectors and their bioactivity upon activation, the anticipated concentration of activator and the responsiveness of the activator site to presence of the activator.

The total amount of protide can be administered as a single dose or by infusion over a relatively short period of time, or can be administered in multiple doses administered over a more prolonged period of time. Such considerations will depend on a variety of case-specific factors such as, for example, whether the disease category is characterized by acute episodes or gradual or chronic deterioration. For an individual affected with an acute infection or inflammatory response, for example, as associated with a bacterial infection, the substance can be administered as a single dose or by infusion of several large doses in a relatively short period of time. For an individual affected with chronic deterioration, for example, as associated with a neuroinflammatory disorder, the substance can be administered in a slow-release matrice, which can be implanted for systemic delivery or at the site of the target tissue, which means an area proximal to the desired context. Contemplated matrices useful for controlled release of therapeutic compounds are well known in the art, and include materials such as DepoFoam™, biopolymers, micropumps, and the like.

The protides administered in the methods of the invention can be administered to the individual by any number of routes known in the art including, for example, systemically, such as intravenously or intraarterially. A therapeutic protide can be provided in the form of isolated and substantially purified polypetides in pharmaceutically acceptable formulations using formulation methods known to those of ordinary skill in the art. These formulations can be administered by standard routes, including for example, topical, transdermal, intraperitoneal, intracranial, intracerebroventricular, intracerebral, intravaginal, intrauterine, oral, rectal or parenteral such as intravenous, intraspinal, intrathecal, subcutaneous or intramuscular routes. Intrathecal administration of a therapeutic protide into the intradural or subarachnoid space can be an appropriate route for decreasing the severity of a neuroinflammatory condition. Intravenous administration of a terhapeutic substance containing a protide also is a preferred route for practicing the invention. In addition, a therapeutic substance administered in the methods of the invention can be incorporated into biodegradable polymers allowing for sustained release of the substance useful for prophylactic and reconstitutive applications described above. Biodegradable polymers and their use are described, for example, in Brem et al., *J. Neurosurg.* 74:441-446 (1991), which is incorporated herein by reference.

The methods for treating a particular pathological condition additionally can be practiced in conjunction with other therapies. For example, for treating cancer, the methods of the invention can be practiced prior to, during, or subsequent to conventional cancer treatments such as surgery, chemotherapy, including administration of cytokines and growth factors, radiation or other methods known in the art. Similarly, for treating pathological conditions which include infectious disease, the methods of the invention can be practiced prior to, during, or subsequent to conventional treatments, such as antibiotic administration, against infectious agents or other methods known in the art. Treatment of pathological conditions of autoimmune disorders also can be accomplished by combining the methods of the invention for inducing an immune response with conventional treatments for the particular autoimmune diseases. Conventional treatments include, for example, chemotherapy, steroid therapy, insulin and other growth factor and cytokine therapy, passive immunity and inhibitors of T cell receptor binding. The protides of the invention can be administered in conjunction with these or other methods known in the art and at various times prior, during or subsequent to initiation of conventional treatments. For a description of treatments for pathological conditions characterized by aberrant cell growth see, for example, *The Merck Manual*, Sixteenth Ed, (Berkow, R., Editor) Rahway, N.J., 1992.

As described above, administration of an invention protide can be, for example, simultaneous with or delivered in alternative administrations with the conventional therapy, including multiple administrations. Simultaneous administration can be, for example, together in the same formulation or in different formulations delivered at about the same time or immediately in sequence. Alternating administrations can be, for example, delivering a protide formulation and a conventional therapeutic treatment in temporally separate administrations. Temporally separate administrations of a compound, immunomodulatory flagellin peptide, polypeptide or modification thereof, and conventional therapy can use different modes of delivery and routes.

A therapeutic protide-containing substance administered in the methods of the invention also can be administered as a solution or suspension together with a pharmaceutically acceptable medium. Such a pharmaceutically acceptable medium can include, for example, sterile aqueous solvents such as sodium phosphate buffer, phosphate buffered saline, normal saline or Ringer's solution or other physiologically buffered saline, or other solvent or vehicle such as a glycol, glycerol, an oil such as olive oil or an injectable organic ester. A pharmaceutically acceptable medium can additionally contain physiologically acceptable compounds that act, for example, stabilize the neutralizing agent, increase its solubility, or increase its absorption. Such physiologically acceptable compounds include, for example, carbohydrates such as glucose, sucrose or dextrans; antioxidants such as ascorbic acid or glutathione; receptor mediated permeabilizers, which can be used to increase permeability of the blood-brain barrier; chelating agents such as EDTA, which disrupts microbial membranes; divalent metal ions such as calcium or magnesium; low molecular weight proteins; lipids or liposomes; or other stabilizers or excipients. Those skilled in the art understand that the choice of a pharmaceutically acceptable carrier depends on the route of administration of the compound containing the protides and on its particular physical and chemical characteristics.

Formulations suitable for parenteral administration include aqueous and non-aqueous sterile injection solutions such as the pharmaceutically acceptable mediums described above. The solutions can additionally contain, for example, buffers, bacteriostats and solutes which render the formulation isotonic with the blood of the intended recipient. Other formulations include, for example, aqueous and non-aqueous sterile suspensions which can include suspending agents and thickening agents. The formulations can be presented in unit-dose or multi-dose containers, for example, sealed ampules and vials, and can be stored in a lyophilized condition requiring, for example, the addition of the sterile liquid carrier, immediately prior to use. Extemporaneous injection solutions and suspensions can be prepared from sterile powders, granules and tablets of the kind previously described.

For applications that require the protide-containing compounds and compositions to cross the blood-brain barrier, formulations that increase the lipophilicity of the compound are particularly desirable. For example, the neutralizing agent can be incorporated into liposomes (Gregoriadis, *Liposome Technology, Vols. I to III,* 2nd ed. (CRC Press, Boca Raton Fla. (1993)). Liposomes, which consist of phospholipids or other lipids, are nontoxic, physiologically acceptable and metabolizable carriers that are relatively simple to make and administer.

A therapeutic protide-containing substance administered in the methods of the invention can also be prepared as nanoparticles. Adsorbing peptide compounds onto the surface of nanoparticles has proven effective in delivering peptide drugs to the brain (see Kreuter et al.; *Brain Research* 674:171-174 (1995). Exemplary nanoparticles are colloidal polymer particles of poly-butylcyanoacrylate with a therapeutic protide-containing substance to be administered in the methods of the invention adsorbed onto the surface and then coated with polysorbate 80.

Image-guided ultrasound delivery of a therapeutic protide-containing substance administered in the methods of the invention through the blood-brain barrier to selected locations in the brain can be utilized as described in U.S. Pat. No. 5,752,515. Briefly, to deliver a therapeutic substance past the blood-brain barrier a selected location in the brain is targeted and ultrasound used to induce a change detectable by imaging in the central nervous system (CNS) tissues and/or fluids at that location. At least a portion of the brain in the vicinity of the selected location is imaged, for example, via magnetic resonance imaging (MRI), to confirm the location of the change. An therapeutic substance administered in the methods of the invention into the patient's bloodstream can be delivered to the confirmed location by applying ultrasound to effect opening of the blood-brain barrier at that location and, thereby, to induce uptake of the substance.

In addition, polypeptides called receptor mediated permeabilizers (RMP) can be used to increase the permeability of the blood-brain barrier to molecules such as therapeutic, prophylactic or diagnostic substances as described in U.S. Pat. Nos. 5,268,164; 5,506,206; and 5,686,416. These receptor mediated permeabilizers can be intravenously co-administered to a host with molecules whose desired destination is the cerebrospinal fluid compartment of the brain, for example, in the treatment of a neuroinflammatory condition. The permeabilizer polypeptides or conformational analogues thereof allow therapeutic substances to penetrate the blood-brain barrier and arrive at their target destination which can be selected based on its proximity to the desired activation context. Such polypeptides can be designed as part of strategic invention protides.

In current treatment regimes for most diseases, more than one compound is often administered to an individual for management of the same or different aspects of the disease. Similarly, in the methods of the invention for treating a vascular injury, neoplastic condition, microbial infection, a condition associated with decreased cell death or inflammatory condition, a therapeutic protide-containing substance can advantageously be formulated with a second therapeutic compound such as an anti-inflammatory compound, antimicrobail compound, chemotherapeutic compound, immunosuppressive compound or any other compound that manages the same or different aspects of the particular disease. As an example, for treatment of an infectious disease a therapeutic substance can advantageously be formulated with a second therapeutic compound such as an antibiotic. Contemplated methods of treating a pathological condition by administering to a subject a therapeutically effective amount of an invention protide therefore include administering a therapeutic substance useful in the methods of the invention alone, in combination with, or in sequence with, such other compounds. Alternatively, combination therapies can consist of fusion proteins, where a therapeutic substance useful for treating a particular pathological condition is linked to a heterologous protein, such as an invention protide. It is understood that modifications which do not substantially affect the activity of the various embodiments of this invention are also included within the definition of the invention provided herein. Accordingly, the following examples are intended to illustrate but not limit the present invention.

EXAMPLE I

Design and Functional Confirmation of Protide-1

This example describes the design of Protide-1 (PT-1), a peptide antibiotide with distinct effector and activator domains. The example further describes the confirmation of activity of PT-1.

PT-1 consists of two effectors and one activator site. In particular, PT-1 contains an antimicrobial peptide effector (RP-1), a chemokine-like peptide effector (IL-8 domain), and an activator site specific for staphylococcal V8 protease, one of numerous virulence factors that is elaborated by *S. aureus* in order to establish and proliferate infection. PT-1 was designed to be cleaved into two distinct effectors in the presence of the activator, staphylococcal V8 protease. In particular, PT-1 was designed to exert antimicrobial activity less than that of the antimicrobial peptide RP-1 in the absence of V8 protease, but antimicrobial activity equivalent to or exceeding that of RP-1 in the presence of V8 protease produced by *S. aureus*. Thus, PT-1 was designed to exert optimal antimicrobial activity in the context of infections due to staphylococcal cells elaborating the virulence factor V8 protease.

Since PT-1 is a peptide antibiotide, it was synthesized entirely by solid-phase peptide synthesis via conventional F-moc synthetic chemistry well known in the art and described in detail elsewhere. PT-1 was synthesized in the Biopolymer Core Facility, Harbor-UCLA REI utilizing a Symphony Multiplex peptide synthesizer and Rainin Instruments. Following peptide chain assembly, the complete PT-1 peptide was cleaved from the resin, precipitated, and washed per standard techniques. Preparative reverse-phase HPLC (RP-HPLC) employing water/acetonitrile gradients containing 0.01% trifluoroacetic acid (TFA) yielded subsequent purification of PT-1, which typically achieved >85% baseline purity. Purified PT-1 was subsequently assessed by analytical RP-HPLC and acid-urea polyacrylamide gel electrophoresis (AU-PAGE) to ensure purity, amino acid analysis and modified Lowry assay to verify quantity, and MALDI-TOF mass spectrometry to corroborate correct synthesis via mass.

Similarly, the antimicrobial peptide RP-1 was synthesized, purified, and verified for purity and correct mass substantially as described in international patent publication WO99/429119, which is incorporated herein by reference in its entirety.

In order to assess the antimicrobial properties of PT-1, a panel of well-characterized test pathogens was used that included *S. aureus* strains ISP479C and ISP479R as described by Dhawan et al., *Infect. Immun.* 66:3576-3479 (1998); *Candida albicans* strains 36082 (ATCC type strain 36082)and 36082R as described by Yeaman et al., *Infect. Immun.* 64:1379-1384 (1996); *Salmonella typhimurium* strains m5996s and 14028s as described by Fields et al., *Science* 243:1059-62 (1989);Yeaman et al., 38*th Interscience Conference on Antimicrobial Agents and Chemotherapy* (ICAAC), San Diego, Calif., Abstract No. F-170 (1999); and *Bacillus subtilis* strain ATCC 6633 as described by Yeaman et al., *Infect. Immun.* 60:1202-1209 (1992), each of which is incorporated herein by reference in its entirety.

In order to compare the antimicrobial activities of PT-1 with those of RP-1 against a panel of test pathogens, radial diffusion assay and a microtiter well assay were utilized.

Briefly, a modified radial diffusion assay was employed to compare the antimicrobial activities of PT-1 with RP-1 in a solid-phase matrix format. In this assay, organisms were introduced at an inoculum of $10^6$ CFU/ml into a solution of 1% (wt/vol) molecular grade agarose and appropriate levels of mM glucose in PIPES buffer (PH 5.5 or 7.5; melted and then cooled to 42° C. prior to introduction of the organisms). The liquid underlayer matrix containing test organism was then vortexed, poured into a petri dish, and allowed to solidify. Wells (4 mm) were removed from the solidified underlayer, into which 10 ul samples of PT-1 or RP-1 were added to achieve a final concentration of 5 ug per well. The reaction plates were subsequently incubated at 37° C. for 3 h, followed by overlay with nutrient or Sabaroud's agar as appropriate for bacterial or fungal test pathogens. The assay plates were then incubated for 18 h at 37° C., after which zones of inhibition (in mm of diameter) were measured and recorded.

A microtiter well assay was also performed as a complement to the radial diffusion assay described above. In this assay, PT-1, RP-1, or V8 protease (Sigma Chemical Co.) were serially diluted from 100 ug (range, 100-0.20 ug/ml) and individually assessed for antimicrobial activity against *S. aureus* strains ISP479C and ISP479R as described above. In addition, this assay allowed for the evaluation of antimicrobial activities of combinations of PT-1 and V8, in conditions of constant or dynamic dilution of one or both agents. This latter approach enabled the determination of static as well as dynamic fractional inhibitory concentrations (FICs) of PT-1 in the presence and absence of purified V8 protease.

When exposed to purified V8 protease in vitro, PT-1 was in a time frame of minutes cleaved (activated) into two separate fragments that were distinguishable upon analytical RP-HPLC as well as acid-urea polyacrylamide gel electrophoresis. These fragments exhibited retention times that were consistent with those of RP-1 and IL-8-like domains that compose the pre-cleaved form of PT-1.

In radial diffusion assays, PT-1 demonstrated substantially less antimicrobial activity than RP-1 against all organisms except *S. aureus*. Therefore, an absence of V8 protease in organisms other than *S. aureus* resulted in no activation of PT-1, consistent with the concept and design of PT-1, since only *S. aureus* elaborates V8 protease. However, activation and enhanced antimicrobial activity of PT-1 was observed for both *S. aureus* strains, regardless of their intrinsic susceptibility or resistance to related antimicrobial agents. This demonstrates that the PT-1 protide is context-activated.

In microtiter assays, PT-1 in the presence of purified V8 protease consistently demonstrated a 2-fold or more increased activity compared to PT-1 in the absence of this activator. For example, when co-incubated with 1 ml V8 protease, PT-1 exerted an MIC against *S. aureus* strains of 3.1 ug/ml, as compared with its MIC of 12.5 without V8 protease. These findings convey an FIC of <0.5, considered to represent a synergistic relationship between PT-1 activation by V8 protease, and enhanced activity of the resulting effector against the test strain.

The above results exemplify the design and functional confirmation of a protide by demonstrating that PT-1 has enhanced antimicrobial activity in the context of V8 protease.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A context-activated protide comprising one activator site and two effector peptides having distinct biological functions, wherein said distinct biological functions are antimicrobial and immunomodulatory, wherein said context-activation results from the association between an enzyme expressed by a bacterial pathogen with said activator site, and wherein said immunomodulatory function comprises mediation of an immune response that is specific for a target antigen or mechanism of pathogenesis.

2. The context-activated protide of claim 1, wherein said context-activation initiates said biological functions of said effectors.

3. The context-activated protide of claim 1, wherein said bacterial pathogen is *S. aureus*.

4. The context-activated protide of claim 1, wherein said *S. aureus* belongs to a methicillin-resistant strain.

5. The context-activated protide of claim 3, wherein said *S. aureus* is selected from the group consisting of a vancomycin-resistant strain and intermediate-resistant to vancomycin strain.

6. The context-activated protide of claim 3, wherein said enzyme is a surface protein transpeptidase (sortase).

7. The protide of claim 1, wherein said antimicrobial function comprises directly killing said bacterial pathogen.

8. The protide of claim 1, wherein said antimicrobial function comprises inhibition of said surface protein transpeptidase (sortase).

9. A context-activated protide comprising one activator site and two effector peptides having distinct biological functions, wherein said distinct biological functions are antimicrobial and immunomodulatory, and wherein said context-activation results from the association between an enzyme expressed by a bacterial pathogen with said activator site, and wherein said immunomodulatory function comprises trafficking cytokine functional groups or immune effector cell types to a site of inflammation.

10. The protide of claim 9, wherein one of said effector peptides comprises interleukin-8, and wherein said other effector peptide comprises Defensin hNP-1, and wherein said activator comprises a protease.

* * * * *

SEQUENCE LISTING

<160> NUMBER OF SEQ ID NOS: 5

<210> SEQ ID NO 1
<211> LENGTH: 33
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 1

Ala Lys Glu Leu Arg Cys Gln Cys Ile Lys Thr Tyr Ser Lys Glu Ala
 1               5                  10                  15

Leu Tyr Lys Lys Phe Lys Lys Lys Leu Leu Lys Ser Leu Lys Arg Leu
            20                  25                  30

Gly

<210> SEQ ID NO 2
<211> LENGTH: 36
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 2

Ala Lys Glu Leu Arg Cys Gln Cys Ile Lys Thr Tyr Ser Lys Leu Ala
 1               5                  10                  15

Arg Ser Ala Leu Tyr Lys Lys Phe Lys Lys Lys Leu Leu Lys Ser Leu
            20                  25                  30

Lys Arg Leu Gly
35

<210> SEQ ID NO 3
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 3

Ala Lys Glu Leu Arg Cys Gln Cys Ile Lys Thr Tyr Ser Lys Leu Val
 1               5                  10                  15

Pro Arg Gly Ser Ala Leu Tyr Lys Lys Phe Lys Lys Lys Leu Leu Lys
            20                  25                  30

Ser Leu Lys Arg Gly
        35

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 4

Ala Lys Glu Leu Arg Cys Gln Cys Ile Lys Thr Tyr Ser Lys Pro Gln
 1               5                  10                  15

Gly Ile Ala Gly Gln Ala Leu Tyr Lys Lys Phe Lys Lys Lys Leu Leu
            20                  25                  30

```
Lys Ser Leu Lys Arg Leu Gly
        35

<210> SEQ ID NO 5
<211> LENGTH: 5
<212> TYPE: PRT
<213> ORGANISM: Escherichia coli
<220> FEATURE:
<221> NAME/KEY: MOD_RES
<222> LOCATION: (3)..(3)
<223> OTHER INFORMATION: Any amino acid

<400> SEQUENCE: 5

Leu Pro Xaa Thr Gly
 1               5
```